United States Patent
He et al.

(10) Patent No.: US 12,109,261 B1
(45) Date of Patent: Oct. 8, 2024

(54) STABILIZED HEMAGGLUTININ (HA) TRIMERS AS INFLUENZA VACCINE ANTIGENS

(71) Applicant: THE SCRIPPS RESEARCH INSTITUTE, La Jolla, CA (US)

(72) Inventors: Linling He, San Diego, CA (US); Jiang Zhu, San Diego, CA (US); Ian A. Wilson, La Jolla, CA (US); Yi-Zong Lee, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 18/670,803

(22) Filed: May 22, 2024

Related U.S. Application Data

(60) Provisional application No. 63/503,725, filed on May 23, 2023.

(51) Int. Cl.
| | |
|---|---|
| *C07K 14/005* | (2006.01) |
| *A61K 39/12* | (2006.01) |
| *A61K 39/145* | (2006.01) |
| *C07K 1/00* | (2006.01) |
| *C07K 14/11* | (2006.01) |
| *A61K 39/00* | (2006.01) |

(52) U.S. Cl.
CPC .......... *A61K 39/145* (2013.01); *C07K 14/005* (2013.01); *A61K 2039/6031* (2013.01); *C12N 2760/16122* (2013.01); *C12N 2760/16134* (2013.01); *C12N 2760/16222* (2013.01); *C12N 2760/16234* (2013.01); *C12N 2760/16322* (2013.01); *C12N 2760/16334* (2013.01)

(58) Field of Classification Search
CPC .............. C07K 14/005; C07K 16/1018; C07K 2317/76; C07K 2319/42; A61P 31/16
See application file for complete search history.

(56) References Cited

PUBLICATIONS

Lee, et al., Receptor Mimicry by Antibody F045-092 Facilitates Universal Binding to the H3 Subtype of Influenza Virus, Nature Communications, Apr. 10, 2014, pp. 1-9.
Milder, et al., Universal Stabilization of the Influenza Hemagglutinin by Structure-based Redesign of the pH Switch Regions, PNAS, 2022, pp. 1-8, vol. 119, No. 6.

*Primary Examiner* — Barry A Chestnut
(74) *Attorney, Agent, or Firm* — Hugh Wang; Thomas Fitting

(57) ABSTRACT

The present invention provides novel engineered influenza hemagglutinin (HA) proteins, related polynucleotide sequences, and vaccine compositions including nanoparticle compositions. Relative to a wildtype HA protein, the engineered HA proteins are stabilized via substitutions of one or more conserved residues in the HA2 ectodomain with hydrophobic residues. The invention also provides methods of using such vaccine compositions in various therapeutic applications, e.g., for preventing or treating influenza viral infections.

23 Claims, 9 Drawing Sheets

Specification includes a Sequence Listing.

Identification of the causes of hemagglutinin (HA) metastability (*based on H3 numbering*)
Alignment of HA2 ectodomains (HA2$_{ECTO}$) from 4 IAVs (H1, H3, H5, and H7) and 2 IBVs

```
H1N1-CA-2009       RLATGLRNIPSIQS----R GLFGAIAGFIEGGWTGMVDGWYGYHHQNEQGSGYAADLKS
H1N1-MI-2015       RLATGLRNVPSIQS----R GLFGAIAGFIEGGWTGMVDGWYGYHHQNEQGSGYAADLKS
H5N1-VN-2004       VLATGLRNSPQRERRRK-KR GLFGAIAGFIEGGWQGMVDGWYGYHHSNEQGSGYAADKES
H5N1-IN-2005       VLATGLRNSPQRESRRK-KR GLFGAIAGFIEGGWQGMVDGWYGYHHSNEQGSGYAADKES
H3N2-HK-1968  HA1  KLATGMRNVPEKQT----R GLFGAIAGFIENGWEGMIDGWYGFRHQNSEGTGQAADLKS
H3N2-KS-2017       KLATGMRNVPERQT----R GIFGAIAGFIENGWEGMVDGWYGFRHQNSEGRGQAADLKS
H7N9-SH-2013       LLATGMKNVPEIPK----GR GLFGAIAGFIENGWEGLIDGWYGFRHQNAQGEGTAADYKS
H7N9-GD-2017       LLATGMKNVPEVPKRKTAR GLFGAIAGFIENGWEGLIDGWYGFRHQNAQGEGTAADYKS
FluB-BB-2008       KLANGTKYRPPAKLLKE--R GFFGAIAGFLEGGWEGMIAGWHGYTSHGAHGVAVAADLKS
FluB-FL-2006       KLANGTKYRPPAKLLKE--R GFFGAIAGFLEGGWEGMIAGWHGYTSHGAHGVAVAADLKS
                   **.*. :  *          *.*******.*.**. *;; *:*.*;    .* . *** .*

K51              N95(IAV)/Q95(IBV)
H1N1-CA-2009       TQNAIDEITN K VNSVIEKMNTQFTAVGKEFNHLEKRIENLNKKVDDGFLDIWTY N AELLV
H1N1-MI-2015       TQNAIDKITN K VNSVIEKMNTQFTAVGKEFNHLEKRIENLNKKVDDGFLDIWTY N AELLV
H5N1-VN-2004       TQKAIDGVTN K VNSIIDKMNTQFEAVGREFNNLERRIENLNKKMEDGFLDVWTY N AELLV
H5N1-IN-2005       TQKAIDGVTN K VNSIIDKMNTQFEAVGREFNNLERRIENLNKKMEDGFLDVWTY N AELLV
H3N2-HK-1968       TQAAIDQING K LNRVIEKTNEKFHQIEKEFSEVEGRIQDLEKYVEDTKIDLWSY N AELLV
H3N2-KS-2017       TQAAIDQING K LNRLIGKTNEKFHQIEKEFSEVEGRIQDLEKYVEDTKIDLWSY N AELLV
H7N9-SH-2013       TQSAIDQITG K LNRLIEKTNQQFELIDNEFNEVEKQIGNVINWTRDSITEVWSY N AELLV
H7N9-GD-2017       TQSAIDQITG K LNRLIAKTNQQFKLIDNEFNEVEKQIGNVINWTRDSITEVWSY N AELLV
FluB-BB-2008       TQEAINKITK N LNSLSELEVKNLQRLSGAMDELHNEILELDEKVDDLRADTISS Q IELAV
FluB-FL-2006       TQEAINKITK N LNSLSELEVKNLQRLSGAMDELHNEILELDEKVDDLRADTISS Q IELAV
                   ** **:  :.   .    :* :     ::  :   ..:..*  :: :  *  :  :.:  ** *

E103      R106(IAV group1)/H106(IAV group 2)/G106(IBV)
H1N1-CA-2009       LL E NE R TLDYHDSNVKNLYEKVRSQLKNNAKEIGNGCFEFYHKCDNTCMESVKNGTYDYPKYSEEAKLNR-EEIDG
H1N1-MI-2015       LL E NE R TLDYHDSNVKNLYEKVRNQLKNNAKEIGNGCFEFYHKCDNTCMESVKNGTYDYPKYSEEAKLNR-EKIDG
H5N1-VN-2004       LM E NE R TLDFHDSNVKNLYDKVRLQLRDNAKELGNGCFEFYHKCDNECMESVRNGTYDYPQYSEEARLKR-EEISG
H5N1-IN-2005       LM E NE R TLDFHDSNVKNLYDKVRLQLRDNAKELGNGCFEFYHKCDNECMESIRNGTYNYPQYSEEARLKR-EEISG
H3N2-HK-1968       AL E NQ H TIDLTDSEMNKLFEKTRRQLRENAEDMGNGCFKIYHKCDNACIESIRNGTYDHDVYRDEALNNR-FQIKG
H3N2-KS-2017       AL E NQ H TIDLTDSEMNKLFEKTKKQLRENAEDMGNGCFKIYHKCDNACMGSIRNGTYDHNVYRDEALNNR-FQIKG
H7N9-SH-2013       AM E NQ H TIDLADSEMDKLYERVKRQLRENAEEDGTGCFEIFHKCDDDCMASIRNNTYDHSKYREEAMQNR-IQIDP
H7N9-GD-2017       AM E NQ H TIDLADSEMDKLYERVKRQLRENAEEDGTGCFEIFHKCDDDCMASIRNNTYDHRKYREEAMQNR-IQIDP
FluB-BB-2008       LL S NE G IINSEDEHLLAERKLKKMLGPSAVEIGNGCFETKHKCNQTCLDRIAAGTFDAGEFSLPTFDSLNITAAS
FluB-FL-2006       LL S NE G IINSEDEHLLAERKLKKMLGPSAVEIGNGCFETKHKCNQTCLDRIAAGTFNAGEFSLPTFDSLNITAAS
                   :  .*:  ::   *.: :  * : *  .* *.***: ***::  *: :  : .*::   :   . .
```

FIG. 3A

Identification of the causes of hemagglutinin (HA) metastability (*based on H3 numbering*)
The fundamental cause of metastability Side View — Side View

N95 — N95

Top View — Top View

N95 — Q95

H1N1-CA-2009 — FluB-BB-2008

FIG. 3B

Identification of the causes of hemagglutinin (HA) metastability (based on H3 numbering)

The secondary cause of metastability

The hypothetical pH sensor

Stabilization of the H1N1 hemagglutinin (HA) trimer by a single mutation (*based on H3 numbering*)

H1N1-CA-2009 HA SEC profiles

FIG. 4A

STABILIZED HEMAGGLUTININ (HA) TRIMERS AS INFLUENZA VACCINE ANTIGENS

CROSS-REFERENCE TO RELATED APPLICATIONS

The subject patent application claims the benefit of priority to U.S. Provisional Patent Application No. 63/503,725 (filed May 23, 2023). The full disclosure of the priority application is incorporated herein by reference in its entirety and for all purposes.

SEQUENCE LISTING

This application includes by incorporation of reference a sequence listing in the XML format, 2157_2_Sequence_Listing, which was created on May 10, 2024 and contains 24 KB in content.

BACKGROUND OF THE INVENTION

Influenza is an acute respiratory illness in humans, with a short incubation period followed by asymptomatic to severe clinical symptoms. Influenza viruses cause epidemics and pandemics, which contribute to 250,000 to 500,000 deaths per year worldwide and impose a global health burden. Influenza viruses belong to the Orthomyxoviridae family and can be classified into four types, A-D. Influenza A and B viruses (IAV and IBV) contain eight, negative-sense, single-stranded viral RNA gene segments, which encode essential viral proteins such as hemagglutinin (HA), neuraminidase (NA), and matrix 2 (M2) protein. In comparison, influenza C and D viruses (ICV and IDV) possess seven viral RNA gene segments as the hemagglutinin-esterase fusion (HEF) protein viral RNA replaces the HA and NA viral RNAs. IAVs are the primary cause of influenza pandemics and a major contributor to the annual influenza epidemics in humans. IAVs use wild aquatic birds as the natural reservoir and can infect other species besides humans, such as pigs. Due to the ability to adapt to and infect various species, IAVs are more diverse than IBVs. Both IAVs and IBVs possess a host-derived lipid membrane, with HA, NA, and M2 decorated on the surface. IAVs can be divided into subtypes based on the genetic and antigenic properties of the surface antigens HA and NA, which mediate viral entry and release, respectively. To date, 18 HA (H1-18) and 9 NA subtypes (N1-11) have been identified that constitute the circulating IAV strains. IAVs can be divided into two phylogenetically distinct groups. Group 1 comprises of H1, H2, H5, H6, H8, H9, H11, H13, H16, H17 and H18 and Group 2 consists of H3, H4, H7, H10, H14 and H15. HA within a subtype has up to 15% sequence diversity, whereas HA subtypes within a group and between two groups have 40% and 60% sequence diversity, respectively. H1N1 (Group 1) and H3N2 (Group 2), as well as two antigenically distinct IBV lineages (Victoria and Yamagata), are used in most seasonal Flu vaccines, with the strain backbones determined by the World Health Organization (WHO) on a yearly basis.

A significant challenge facing the influenza vaccine development is the constant evolution of the surface antigens (HA and NA) in response to pressure from the host immune system, known as antigenic drift and antigenic shift. Antigenic drift is evident in circulating seasonal IAVs, where mutations in the surface antigens enable reinfection of the same host, whereas antigenic shift is caused by the less frequent reassortment events and is responsible for the pandemics. The HA protein is the main target of humoral response. Hundreds of neutralizing antibodies (NAbs) have been isolated from infected or vaccinated individuals. Some broadly neutralizing antibodies (bNAbs) can block IAVs of diverse HA subtypes or react with both IAVs and IBVs. The HA proteins of IAVs and IBVs adopt the same protein fold despite their low sequence identity. The structural analysis of HA in complex with NAbs and bNAbs has identified a number of neutralizing epitopes in the head, in the stem, and at their interface. In general, the stem contains more conserved epitopes than the head. But the head does contain some conserved epitopes present in diverse strains within one HA subtype or across multiple HA subtypes. The head epitopes are located in the receptor-binding site (RBS) or outside the RBS, with the RBS being the major target of vaccine-induced antibody responses. Currently, wildtype HAs are used in all seasonal influenza vaccines and recombinant HA-based vaccines under preclinical development.

In spite of the substantial progresses in influenza vaccine design, there are still needs in the medical field for more effective and potent vaccine immunogens, e.g., for preventing influenza viral infections. The present invention addresses such unmet needs in the art.

SUMMARY OF THE INVENTION

In one aspect, the invention provides engineered influenza viral hemagglutinin (HA) proteins. These proteins contain a modified HA2 ectodomain that has substitution of the amino acid residue at position 95 or at position 106 with a hydrophobic residue. Numbering of the amino acids in HA2 is based on influenza A Subtype H3. In addition to the modified HA2 ectodomain, some of the engineered influenza HA proteins also contain an intact HA1 protein, which some others do not contain the HA head domain. Some of the engineered influenza HA proteins are based on a type A influenza virus, and the substituted residue in HA2 is N95. Some of the engineered influenza HA proteins are based on a type B influenza virus, and the substituted residue in HA2 is Q95. Some of the engineered influenza HA proteins are based on a type C influenza virus, and the substituted residue in HA2 is E95.

In various embodiments, the conserved residue at position 95 or position 106 in HA2 can be replaced with Ala, Val, Leu, Ile, Met, Phe, Tyr, or Trp. Some engineered influenza HA proteins of the invention contain a modified HA2 ectodomain that has substitutions of both amino acid residue at positions 95 and 106 with a hydrophobic residue. In some of these embodiments, the substitution at each position is independently with Ala, Val, Leu, Ile, Met, Phe, Tyr, or Trp. Some of these engineered influenza HA proteins are based on a Group 1 influenza A virus, and the replaced residue at position 106 is R106. Some of these engineered influenza HA proteins are based on a Group 2 influenza A virus, and the replaced residue at position 106 is H106. Some of these engineered influenza HA proteins are based on an influenza B virus, and the replaced residue at position 106 is G106. In these embodiments, the substitution at each position is independently with Ala, Val, Leu, Ile, Met, Phe, Tyr, or Trp.

Some engineered influenza HA proteins of the invention contain a modified HA2 ectodomain that has (1) substitution at position 95 with a hydrophobic residue, and (2) additional amino acid substitution at one or both of positions 51 and 103 with a hydrophobic residue. In some of these embodiments, the HA protein is based on an influenza A virus, and the additionally substituted amino acid residues are K51 and E103.

In some embodiments, the engineered influenza HA protein of the invention can additionally contain the subunit sequence of a self-assembling nanoparticle that is fused to the C-terminus of the engineered HA protein.

In some related aspects, the invention provides (1) pharmaceutical compositions that contain an engineered influenza HA protein described herein and a pharmaceutically acceptable carrier, (2) polynucleotides encoding the engineered influenza HA proteins described herein. (3) vectors that contain one of the polynucleotides encoding the engineered influenza HA proteins described herein; and (4) host cells that harbor one polynucleotide encoding an engineered influenza HA proteins described herein or a vector containing the polynucleotide. In some pharmaceutical compositions of the invention, the engineered HA protein is displayed on the surface of a self-assembling nanoparticle.

In another aspect, the invention provides influenza viral vaccine compositions containing an engineered HA protein described herein that is displayed on the surface of a self-assembling nanoparticle. In some embodiments, the self-assembling nanoparticle is comprised of a trimeric sequence, and the C-terminus of the engineered HA protein is fused to N-terminus of the subunit sequence of the nanoparticle. In some embodiments, the self-assembling nanoparticle scaffold sequence is I3-01, E2p or ferritin. In some embodiments, the scaffolded vaccine additionally contain a locking domain and/or a T-cell epitope that is fused to the C-terminus of the nanoparticle subunit sequence.

In still another aspect, the invention provides therapeutic methods or uses of treating or preventing an influenza viral infection in a subject. The methods or uses entail administering to the subject a pharmaceutical composition containing an engineered influenza HA protein or a nanoparticle vaccine composition described herein.

A further understanding of the nature and advantages of the present invention may be realized by reference to the remaining portions of the specification and claims.

DESCRIPTION OF THE DRAWINGS

FIGS. 3A-3D show identification of the causes of hemagglutinin metastability. Shown in FIG. 3A is alignment of HA2 ectodomain sequences of 10 HAs from four IAV subtypes (H1, H3, H5 and H7) and 2 IBV lineages (Victoria and Yamagata), SEQ ID NOs: 11-20.

FIGS. 4A-4B show stabilization of the H1N1 hemagglutinin (HA) trimer protein by a single amino acid mutation at N95.

DETAILED DESCRIPTION

I Overview

Figure 1A:
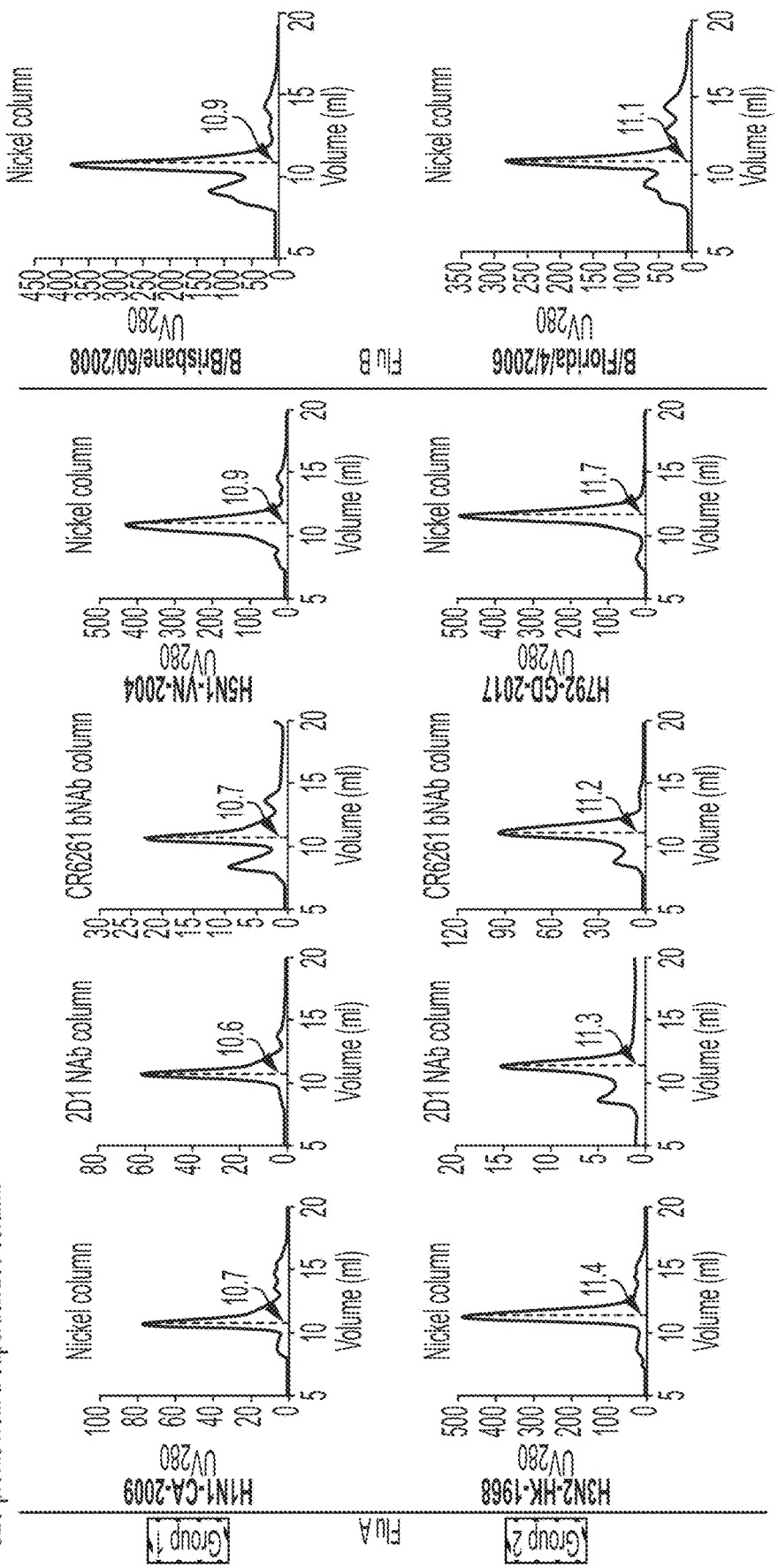
FIGS. 1A-1C show results from analysis of hemagglutinin (HA) metastability.

The subject invention is predicated in part on studies undertaken by the present inventors to explore the causes of influenza viral hemagglutinin (HA) metastability. As a class I viral fusion protein, HA has inherent metastability, which results in a subpar immune response to vaccination. As detailed herein, the inventors first found that the HA trimer could disassemble or show a high level of flexibility in the head or stem. The inventors then identified critical residues in HA2 as potential causes of HA metastability. Based on the H3 numbering system, residue 95, which is Asn (N) in IAV HAs (e.g., A/California/04/2009 H1N1, GenBank Accession Nos: FJ966082 and ACP41105), Gln (Q) in IBV HAs (e.g., B/Brisbane/60/2008, GenBank Accession Nos: FJ766840 and ACN29380), and Glu (E) in ICV HAs (e.g., C/Johannesburg/1/1966, GenBank Accession Nos: AM410041 and CAL69520), is highly conserved among different influenza types and sub-types. The inventors further demonstrated that a single mutation at position 95 of HA2 (e.g., N95L for IAVs) can stabilize the HA trimer of A/California/07/2009 H1N1—a pandemic strain with an unstable HA—in a closed prefusion trimer conformation, as shown by the negative-stain EM analysis. This mutation enabled the purification of H1N1-CA-2009 HA trimer by a head NAb and by a stem bNAb, the latter of which preferably binds the trimeric conformation. For IAVs, this mutation can be combined with a hydrophobic mutation at R106 (IAV, A/California/04/2009 H1N1, GenBank: FJ966082), or hydrophobic mutations at K51 and E103 (a hypothetic pH sensor, numbering according to Milder et al, Proc. Natl. Acad. Sci. USA 2022, 119: e2115379119), to further stabilize the HA trimer. The N95/Q95 mutation-containing HA provides a superior antigen for influenza A/B vaccine development regardless of the delivery system. In addition, these mutations can be used to stabilize headless or stem-only HA antigens for vaccine development.

In accordance with these studies, the invention provides engineered and stabilized influenza HA trimer sequences, in the forms of protein or nucleic acid (DNA/mRNA) or carried by a viral vector, can be used as influenza vaccines. In related embodiments, the invention provides VLP-type influenza vaccines that contain nanoparticles presenting stabilized HA trimers and stem antigens. Influenza vaccines based on the invention have various technical advantages. The hydrophobic mutation at position 95 can stabilize HA trimers from diverse influenza types/subtypes/strains, thus providing a universal solution for HA stabilization. As shown for the A/California/04/09 HA, which disassociates into monomers easily in the soluble form, a single N95L mutation is sufficient to stabilize the HA trimer regardless of the purification method used. Given the low pH condition (pH=5.5) used in the negative-stain EM analysis, the observed structural stability suggests that the N95L-containing HA proteins are also resistant to low pH. In related embodiments, the vaccines can have engineered HA proteins that combine a hydrophobic mutation at position 95 and other mutations in the HA2 ectodomain such as (1) a hydrophobic mutation at position 106 or (2) hydrophobic mutations at K51 and E103 (Milder et al, Proc. Natl. Acad. Sci. USA 2022, 119: e2115379119). This could lead to further increased stability and reduced pH senility of diverse HA trimers.

Vaccines based on the engineered HA sequences can be delivered by different platforms (DNA, mRNA, vector, protein, and nanoparticle) as influenza vaccines. The stabilized HA trimers and stem antigens, in both soluble forms and particulate forms, can be readily produced in ExpiCHO cells with reasonable yield. Since CHO is one of the principal mammalian cell lines used for industrial manufacture of protein therapeutics and vaccines and ExpiCHO is a transient version of this CHO cell line, influenza vaccines obtained from ExpiCHO cells are expected to have the same properties as those from industrial CHO cell lines. This will enable the GMP manufacturing of stabilized HA trimers, stem antigens, and their nanoparticles for human use.

Unless otherwise specified herein, the engineered influenza HA proteins or immunogens of the invention, the encoding polynucleotides, expression vectors and host cells, as well as the related therapeutic applications, can all be generated or performed in accordance with the procedures exemplified herein or routinely practiced methods well known in the art. See, e.g., Methods in Enzymology, Volume 289: Solid-Phase Peptide Synthesis, J. N. Abelson, M. I. Simon, G. B. Fields (Editors), Academic Press; 1st edition (1997) (ISBN-13:978-0121821906); U.S. Pat. Nos. 4,965,343, and 5,849,954; Sambrook et al., Molecular Cloning: A Laboratory Manual, Cold Spring Harbor Press, N.Y., (3rd ed., 2000); Brent et al., Current Protocols in Molecular Biology, John Wiley & Sons, Inc. (ringbou ed., 2003); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998). The following sections provide additional guidance for practicing the compositions and methods of the present invention.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: Academic Press Dictionary of Science and Technology, Morris (Ed.), Academic Press (1$^{st}$ ed., 1992); Oxford Dictionary of Biochemistry and Molecular Biology, Smith et al. (Eds.), Oxford University Press (revised ed., 2000); Encyclopaedic Dictionary of Chemistry, Kumar (Ed.), Anmol Publications Pvt. Ltd. (2002); Dictionary of Microbiology and Molecular Biology, Singleton et al. (Eds.), John Wiley & Sons (3$^{rd}$ ed., 2002); Dictionary of Chemistry, Hunt (Ed.), Routledge (1$^{st}$ ed., 1999); Dictionary of Pharmaceutical Medicine, Nahler (Ed.), Springer-Verlag Telos (1994); Dictionary of Organic Chemistry, Kumar and Anandand (Eds.), Anmol Publications Pvt. Ltd. (2002); and A Dictionary of Biology (Oxford Paperback Reference), Martin and Hine (Eds.), Oxford University Press (4$^{th}$ ed., 2000). Further clarifications of some of these terms as they apply specifically to this invention are provided herein.

As used herein, the singular forms "a," "an," and "the," refer to both the singular as well as plural, unless the context clearly indicates otherwise. For example, "an Env-derived trimer" can refer to both single or plural Env-derived trimer molecules, and can be considered equivalent to the phrase "at least one Env-derived trimer."

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein. Unless otherwise noted, the term "vaccine immunogen" is used interchangeably with "protein antigen" or "immunogen polypeptide."

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For polypeptide sequences, "conservatively modified variants" refer to a variant which has conservative amino acid substitutions, amino acid residues replaced with other amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Epitope refers to an antigenic determinant. These are particular chemical groups or peptide sequences on a molecule that are antigenic, such that they elicit a specific immune response, for example, an epitope is the region of an antigen to which B and/or T cells respond. Epitopes can be formed both from contiguous amino acids or noncontiguous amino acids juxtaposed by tertiary folding of a protein.

Effective amount of a vaccine or other agent that is sufficient to generate a desired response, such as reduce or eliminate a sign or symptom of a condition or disease, such as seasonal flu. For instance, this can be the amount necessary to inhibit viral replication or to measurably alter outward symptoms of the viral infection, such as increase of T cell counts in the case of an influenza infection. In general, this amount will be sufficient to measurably inhibit viral replication or infectivity. When administered to a subject, a dosage will generally be used that will achieve target tissue concentrations (for example, in lymphocytes) that has been shown to achieve in vitro inhibition of viral replication. In some embodiments, an "effective amount" is one that treats (including prophylaxis) one or more symptoms and/or underlying causes of any of a disorder or disease, for example to treat influenza infection. In some embodiments, an effective amount is a therapeutically effective amount. In some embodiments, an effective amount is an amount that prevents one or more signs or symptoms of a particular disease or condition from developing, such as one or more signs or symptoms associated with the disease.

As used herein, a fusion protein is a recombinant protein containing amino acid sequence from at least two unrelated proteins that have been joined together, via a peptide bond, to make a single protein. The unrelated amino acid sequences can be joined directly to each other or they can be joined using a linker sequence. As used herein, proteins are unrelated, if their amino acid sequences are not normally found joined together via a peptide bond in their natural environment(s) (e.g., inside a cell). For example, the amino acid sequences of bacterial enzymes such as *B. stearothermophilus* dihydrolipoyl acyltransferase (E2p) and the amino acid sequences of influenza HA proteins are not normally found joined together via a peptide bond.

Immunogen is a protein or a portion thereof that is capable of inducing an immune response in a mammal, such as a mammal infected or at risk of infection with a pathogen. Administration of an immunogen can lead to protective immunity and/or proactive immunity against a pathogen of interest.

Immune response refers to a response of a cell of the immune system, such as a B cell, T cell, or monocyte, to a stimulus. In some embodiments, the response is specific for a particular antigen (an "antigen-specific response"). In some embodiments, an immune response is a T cell response, such as a CD4+ response or a CD8+ response. In some other embodiments, the response is a B cell response, and results in the production of specific antibodies.

Immunogenic composition refers to a composition comprising an immunogenic polypeptide that induces a measurable CTL response against virus expressing the immunogenic polypeptide, or induces a measurable B cell response (such as production of antibodies) against the immunogenic polypeptide.

As used herein, amino acid numbering or amino acid numbering system refers to the numbering or linear positions of amino acid residues in an HA protein (or a HA1 or HA2 protein) from a prototype influenza strain. With a normalized sequence alignment, it allows comparison of the sequences of different HA proteins (or HA1 or HA2 protein) from other influenza strains or engineered HA proteins described herein with that of the prototype sequence. Utilizing such a standard or normalized amino acid numbering, conserved amino acid residues in the HA proteins from various viral strains or engineered HA proteins can be readily identified and designated. For example, unless otherwise noted herein, amino acid renumbering of the HA2 protein can be based on the HA2 sequence of IAV H3 subtype viruses, e.g., the A/Victoria/361/2011 H3N2 strain exemplified herein. In some embodiments, numbering of the HA protein may be based on the sequence of any of the well-known viral strains, the pandemic causing A/California/04/2009 H1N1 strain or other influenza strains described herein.

Sequence identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

Homologs or orthologs of nucleic acid or amino acid sequences possess a relatively high degree of sequence identity/similarity when aligned using standard methods. Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237-44, 1988; Higgins & Sharp, CABIOS 5:151-3, 1989; Corpet et al., Nuc. Acids Res. 16:10881-90, 1988; Huang et al. Computer Appls. in the Biosciences 8, 155-65, 1992; and Pearson et al., Meth. Mol. Bio. 24:307-31, 1994. Altschul et al., J. Mol. Biol. 215:403-10, 1990, presents a detailed consideration of sequence alignment methods and homology calculations.

The term "subject" refers to any animal classified as a mammal, e.g., human and non-human mammals. Examples of non-human animals include dogs, cats, cattle, horses, sheep, pigs, goats, rabbits, etc. Unless otherwise noted, the terms "patient" or "subject" are used herein interchangeably. Preferably, the subject is human.

The term "treating" or "alleviating" includes the administration of compounds or agents to a subject to prevent or delay the onset of the symptoms, complications, or biochemical indicia of a disease (e.g., an influenza infection), alleviating the symptoms or arresting or inhibiting further development of the disease, condition, or disorder. Subjects in need of treatment include those already suffering from the disease or disorder as well as those being at risk of developing the disorder. Treatment may be prophylactic (to prevent or delay the onset of the disease, or to prevent the manifestation of clinical or subclinical symptoms thereof) or therapeutic suppression or alleviation of symptoms after the manifestation of the disease.

Vaccine refers to a pharmaceutical composition that elicits a prophylactic or therapeutic immune response in a subject. In some cases, the immune response is a protective immune response. Typically, a vaccine elicits an antigen-specific immune response to an antigen of a pathogen, for example a viral pathogen, or to a cellular constituent correlated with a pathological condition. A vaccine may include a polynucleotide (such as a nucleic acid encoding a disclosed antigen), a peptide or polypeptide (such as a disclosed antigen), a virus, a cell or one or more cellular constituents. In some embodiments of the invention, vaccines or vaccine immunogens or vaccine compositions are expressed from fusion constructs and self-assemble into nanoparticles displaying an immunogen polypeptide or protein on the surface.

An influenza vaccine refers to an immunogenic composition capable of stimulating an immune response, administered for the prevention, amelioration, or treatment of influenza virus infection. An influenza vaccine may include, for example, attenuated or killed (e.g., split) influenza virus, virus-like particles (VLPs) and/or antigenic polypeptides (e.g., the engineered hemagglutinins described herein) or DNA derived from them, or any recombinant versions of such immunogenic materials.

Virus-like particle (VLP) refers to a non-replicating, viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art. The presence of VLPs following recombinant expression of viral proteins can be detected using conventional techniques known in the art, such as by electron microscopy, biophysical characterization, and the like. See, for example, Baker et al. (1991) Biophys. J. 60:1445-1456; and Hagensee et al. (1994) J. Virol. 68:4503-4505. For example, VLPs can be isolated by density gradient centrifugation and/or identified by characteristic density banding. Alternatively, cryoelectron microscopy can be performed on vitrified aqueous samples of the VLP preparation in question, and images recorded under appropriate exposure conditions.

A self-assembling nanoparticle refers to a ball-shape protein shell with a diameter of tens of nanometers and well-defined surface gemoetry that is formed by identical copies of a non-viral protein capable of automatically assembling into a nanoparticle with a similar appearance to VLPs. Known examples include ferritin (FR), which is conserved across species and forms a 24-mer, as well as *B. stearothermophilus* dihydrolipoyl acyltransferase (E2p), *Aquifex* aeolicus lumazine synthase (LS), and *Thermotoga maritima* encapsulin, which all form 60-mers. Self-assembling nanoparticles can form spontaneously upon recombinant expression of the protein in an appropriate expression system. Methods for nanoparticle production, detection, and characterization can be conducted using the same techniques developed for VLPs.

III. Engineered Influenza Viral Hemagglutinin (HA) Proteins

The invention provides engineered or redesigned influenza viral hemagglutinin (HA) proteins or polypeptides (as well as polynucleotide sequences) for producing influenza viral vaccines. As a class I viral fusion protein, HA plays an important role in viral entry by binding to the host receptor, sialylated glycans on endothelial cells in the respiratory tract, and by facilitating membrane fusion in the low pH environment of the endosomal compartments after cell entry via endocytosis. During virus replication, HA is first expressed as a precursor protein, a non-covalent homotrimer called HA0. The uncleaved HA0 is cleaved by cellular proteases into HA1 and HA2, which form the functional HA spike on the virion surface. Each monomer of the HA protein consists of a globular head domain and a membrane-proximal stem or stalk domain. The head domain consists of a part of HA1 only (including the receptor-binding domain and vestigial esterase domain), whereas the stem domain contains parts of both HA1 and HA2.

Relative to wildtype HA proteins, the engineered HA proteins or vaccine antigens of the invention bear one or more of the specific modifications in HA2 as detailed herein. They can be derived from the HA protein from any influenza viruses. The HA sequence in which HA2 is modified can be an intact HA protein, a sequence that is substantially identical to a wildtype HA protein, or a variant or fragment of an intact HA protein (e.g., a headless HA). A wide variety of HA sequences from influenza isolates are known in the art. For example, the National Center for Biotechnology Information (NCBI) maintains a database that contains thousands to tens of thousands of complete HA polypeptide sequences for each influenza type or subtype. Utilizing this database, the skilled artisan can readily identify sequences that are suitable for practice of the invention. Thus, suitable HA sequences can include, e.g., wildtype or variant HA polypeptides or polynucleotide sequences of IAVs (H1-H18), IBVs, ICVs and IDVs. In various embodiments, they can be derived from HAs of influenza viruses that mediate infection of different hosts, e.g., human as well as non-human species.

In general, the engineered HA proteins of the invention contain stabilizing mutations in HA2. In some embodiments, the engineered HA proteins contain the entire HA1 protein and a modified HA2 ectodomain. In some other embodiments, the engineered HA proteins can be a headless or stem-only HA protein that contains a modified HA2 ectodomain but not the intact HA1 protein. Typically, the stabilizing mutations in the modified HA2 protein are one or more single amino acid substitutions. In some preferred embodiments, the mutations include substitutions with a hydrophobic residue for (1) the amino acid residue at the HA2 position 95 (or equivalent position in diverse HA sequences) and/or (2) the amino acid residue at the HA2 position 106 (or equivalent position in diverse HA sequences). Unless otherwise indicated, amino acid numbering of a given HA2 protein is based on Influenza A Subtype H3. One example of H3 HA protein structure is PDB 4O5N, which is a crystal structure of hemagglutinin of influenza virus strain A/Victoria/361/2011 (H3N2) (Accession No. AGB08328; SEQ ID NO: 2). Sec, e.g., Lee et al., Nat. Commun. 5:3614, 2014. The HA2 portion of this HA sequence is shown in SEQ ID NO:6. Because the atomic structure was first determined by crystallography for an H3N2 HA protein, historically the H3N2 HA has been used as a template to determine the residue numbers for structures of other HA proteins. Therefore, given this H3-based amino acid numbering system, corresponding amino acid residues that are conserved in and bordering the various domains (e.g., HA2 ectodomain), regions (e.g., head and stem) and structural motifs of an HA protein from any other influenza virus can be readily determined (e.g., by sequence alignment) or otherwise already known in the art. It should be noted that there is a substantial sequence conservation among the HA2 proteins from different influenza virus types and different strains of the same virus type. Therefore, the H3-numbering system is particularly accurate for identification of conserved amino acid positions in the HA2 proteins.

Specifically, the sequence and structure of HA2 are conserved across all viruses (esp. Types A, B, and C, and likely Type D even though very little structural information on D has been reported). As is well characterized in the literature, the HA2 protein is highly conserved across influenza stains, any conserved residue in the protein structure (e.g., N95) of different influenza viruses will be at the same position based on the H3 numbering system. See, e.g., Heiny et al., PLOS ONE 2007, 2 (11): e1190; Fouchier et al., J. Virol. 2005; 79:2814-2822; Nobusawa et al., Virology 1991; 182:475-485; Okuno et al., J. Virol. 1993; 67:2552-2558; and Chun et al., Vaccine 2008, 26:6068-6076. As such, amino acid numbering in HA2 of subtype H3 can be applied to any other viral types and subtypes. For example, residue at position 95 in HA2 is conserved across all IAVs, IBVs, and ICVs. Specifically, the residue at position 95 is N95 for IAVs, Q95 for IBVs, and E95 for ICVs. In addition to the HA2 sequence of the above-noted IAV H3N2 strain (SEQ ID NO:6), the highly conserved nature of position 95 is also evident in the amino acid sequences of the HA2 portion of the HA protein from 3 other exemplified viral strains, IAV strain A/California/04/2009 H1N1, IBV strain B/Brisbane/60/2008 and ICV strain C/Johannesburg/1/1966 (SEQ ID NOs: 5, 7 and 8, respectively. Similar to position 95, the other HA2 amino acid positions for substitution in the engineered HA proteins of the invention are also highly conserved among different influenza viruses. For example, residue at position 106 is R106 for group 1 IAVs, H106 for group 2 IA Vs, and G106 for IBVs.

As alternatives to H3 based HA2 numbering noted above, the conserved residues to be modified in the HA2 ectodomain may also be numbered based on other prototype viral sequences. For example, the two HA2 positions noted above, 95 and 106, are respectively positions 439 and 450 in the full length HA protein sequence of the prototype IAV strain A/California/04/2009 H1N1 (Accession No. ACP41105; SEQ ID NO: 1). Corresponding positions of these highly conserved residues in the HA proteins of other IAVs, as well as HA proteins of other types of influenza viruses such as IBVs and ICVs, can be readily determined via sequence alignment, as exemplified herein in FIG. 3A. As exemplification, residue N439 in the HA protein of this protype H1N1 strain (i.e., N95 based on the H3 HA2 numbering) corresponds to residue N440 in the HA protein of IAV H3N2 strain A/Victoria/361/2011 noted above, residue Q457 in the HA protein of a prototype IBV strain B/Brisbane/60/2008 (Accession No. ACN29380; SEQ ID NO:3), and residue E464 in the HA protein of a ICV strain C/Johannesburg/1/1966 (Accession No. CAL69520; SEQ ID NO:4).

As noted above, some engineered HA proteins of the invention contain just the HA2 ectodomain as opposed to the entire HA2 protein. Sequence of HA2 ectodomain from an influenza virus can be readily ascertained by, e.g., sequence alignment. For example, the wildtype HA2 ectodomain sequences of the exemplified IAV H1N1 strain A/California/04/2009 and IAV H3N2 strain A/Victoria/361/2011 are shown in SEQ ID NOs: 9 and 10, respectively. The boundary of the HA2 ectodomain in several other prototype influenza virus strains described herein can also be readily determined, including that of IAV A/Hong Kong/1/1968 H3N2 (GenBank: CY044261), IAV A/Viet Nam/1203/2004 H5N1 (GenBank: AY818135) and IAV A/Guangdong/HP001/2017 H7N9 (GenBank: KY643843).

In some embodiments, the engineered HA proteins of the invention contain an HA2 ectodomain with substitution at position 95. The residue at this position in the HA2 ectodomain (e.g., N95, Q95 or E95) can be replaced with any hydrophobic residue. One specific engineered HA protein exemplified herein is derived from IAV H1N1 strain A/California/04/2009, which contains HA1 and HA2 ectodomain with a N95L substitution (see Example 3). As demonstrated herein, this single substitution is sufficient to effectively stabilize HA in a closed trimer conformation. In some other embodiments, the engineered HA proteins of the invention can have a substitution at position 106. The residue at this position in the HA2 ectodomain (e.g., R106, H106 or G106) can also be replaced with any hydrophobic residue. Still some other engineered HA proteins of the invention have substitutions at both positions 95 and 106. In these embodiments, each residue at these two positions can be replaced with any hydrophobic residue. In various embodiments, the substituting amino acid residues for each of positions 95 and 106 can independently be Ala, Val, Leu, Ile, Met, Phe, Tyr, or Trp.

Other than the amino acid substitutions at position 95 and/or 106, some engineered HA proteins of the invention can also have substitutions at additional positions in HA2. In some of these embodiments, the additional substitutions include at least one substitution at positions 51 and 103 with a hydrophobic residue. In some embodiments, the engineered HA proteins contain additional substitutions at both residues 51 and 103 with hydrophobic residues. As demonstrated herein, these additional modification of the HA2 ectodomain further increases the stability and reduces pH senility of HA trimers. As a specific exemplification, the engineered HA proteins can contain substitutions at N95, K51 and E103, each with a hydrophobic amino acid residue.

```
SEQ ID NO: 1:
HA of IAV A/California/04/2009 H1N1 sequence
(Accession No. ACP41105; Garten et al., Science
325 (5937), 197-201, 2009):
MKAILVVLLY TFATANADTL CIGYHANNST DTVDTVLEKN

VTVTHSVNLL EDKHNGKLCKLRGVAPLHLG KCNIAGWILG

NPECESLSTA SSWSYIVETP SSDNGTCYPG DFIDYEELRE

QLSSVSSFER FEIFPKTSSW PNHDSNKGVT AACPHAGAKS

FYKNLIWLVK KGNSYPKLSK SYINDKGKEV LVLWGIHHPS

TSADQQSLYQ NADTYVFVGS SRYSKKFKPE IAIRPKVRDQ

EGRMNYYWTL VEPGDKITFE ATGNLVVPRY AFAMERNAGS

GIIISDTPVH DCNTTCQTPK GAINTSLPFQ NIHPITIGKC

PKYVKSTKLR LATGLRNIPS IQSRGLFGAI AGFIEGGWTG

MVDGWYGYHH QNEQGSGYAA DLKSTQNAID EITNKVNSVI

EKMNTQFTAV GKEFNHLEKR NLNKKVDD GFLDIWTYNA

ELLVLLENER TLDYHDSNVK NLYEKVRSQL KNNAKEIGNG

CFEFYHKCDN TCMESVKNGT YDYPKYSEEA KLNREEIDGV

KLESTRIYQI LAIYSTVASS LVLVVSLGAI SFWMCSNGSL

QCRICI

SEQ ID NO: 5: HA2 portion of SEQ ID NO: 1:
GLFGAI AGFIEGGWTG MVDGWYGYHH QNEQGSGYAA DLKSTQNAID

EITNKVNSVI EKMNTQFTAV GKEFNHLEKR IENLNKKVDD

GFLDIWTYNA ELLVLLENER TLDYHDSNVK NLYEKVRSQL

KNNAKEIGNG CFEFYHKCDN TCMESVKNGT YDYPKYSEEA

KLNREEIDGV KLESTRIYQI LAIYSTVASS LVLVVSLGAI

SFWMCSNGSL QCRICI

SEQ ID NO: 9:
HA2 ectodomain portion of SEQ ID NO: 1:
GLFGAI AGFIEGGWTG MVDGWYGYHH QNEQGSGYAA DLKSTQNAID

EITNKVNSVI EKMNTQFTAV GKEFNHLEKR IENLNKKVDD

GFLDIWTYNA ELLVLLENER TLDYHDSNVK NLYEKVRSQL

KNNAKEIGNG CFEFYHKCDN TCMESVKNGT YDYPKYSEEA

KLNREEID

SEQ ID NO: 2:
HA of IAV A/Victoria/361/2011 (H3N2) (Accession
No. AGB08328):
MKTIIALSHI LCLVFAQKLP GNDNSTATLC LGHHAVPNGT

IVKTITNDQI EVTNATELVQ NSSIGEICDS PHQILDGENC

TLIDALLGDP QCDGFQNKKW DLFVERSKAY SNCYPYDVPD

YASLRSLVAS SGTLEFNNES FNWTGVTQNG TSSACIRRSN

NSFFSRLNWL TQLNFKYPAL NVTMPNNEQF DKLYIWGVHH

PVTDKDQIFL YAQSSGRITV STKRSQQAVI PNIGYRPRIR
```

```
NIPSRISIYW TIVKPGDILL INSTGNLIAP RGYFKIRSGK

SSIMRSDAPI GKCNSECITP NGSIPNDKPF QNVNRITYGA

CPRYVKQSTL KLATGMRNVP EKQTRGIFGA IAGFIENGWE

GMVDGWYGFR HQNSEGRGQA ADLKSTQAAI DQINGKLNRL

IGKTNEKFHQ IEKEFSEVEG RIQDLEKYVE DTKIDLWSYN

AELLVALENQ HTIDLTDSEM NKLFEKTKKQ LRENAEDMGN

GCFKIYHKCD NACIGSIRNG TYDHDVYRDE ALNNRFQIKG

VELKSGYKDW ILWISFAISC FLLCVALLGF IMWACQKGNI RCNICI

SEQ ID NO: 6: HA2 portion of SEQ ID NO: 2
GIFGA IAGFIENGWE GMVDGWYGFR HQNSEGRGQA ADLKSTQAAI

DQINGKLNRL IGKTNEKFHQ IEKEFSEVEG RIQDLEKYVE

DTKIDLWSYN AELLVALENQ HTIDLTDSEM NKLFEKTKKQ

LRENAEDMGN GCFKIYHKCD NACIGSIRNG TYDHDVYRDE

ALNNRFQIKG VELKSGYKDW ILWISFAISC FLLCVALLGF

IMWACQKGNI RCNICI

SEQ ID NO: 10:
HA2 ectodomain portion of SEQ ID NO: 2
GIFGA IAGFIENGWE GMVDGWYGFR HQNSEGRGQA ADLKSTQAAI

DQINGKLNRL IGKTNEKFHQ IEKEFSEVEG RIQDLEKYVE

DTKIDLWSYN AELLVALENQ HTIDLTDSEM NKLFEKTKKQ

LRENAEDMGN GCFKIYHKCD NACIGSIRNG TYDHDVYRDE

ALNNRFQIK

SEQ ID NO: 3:
HA of IBV B/Brisbane/60/2008 (Accession No.
ACN29380)
MKAIIVLLMV VTSNADRICT GITSSNSPHV VKTATQGEVN

VTGVIPLTTT PTKSHFANLK TETRGKLCP KCLNCTDLDV

ALGRPKCTGK IPSARVSILH EVRPVTSGCF PIMHDRTKIR

QLPNLLRGYE HIRLSTHNVI NAENAPGGPY KIGTSGSCPN

ITNGNGFFAT MAWAVPKNDK NKTATNPLTI EVPYICTEGE

DQITVWGFHS DNETQMAKLY GDSKPQKFTS SANGVTTHYV

SQIGGFPNQT EDGGLPQSGR IVVDYMVQKS GKTGTITYQR

GILLPQKVWC ASGRSKVIKG SLPLIGEADC LHEKYGGLNK

SKPYYTGEHA KAIGNCPIWV KTPLKLANGT KYRPPAKLLK

ERGFFGAIAG FLEGGWEGMI AGWHGYTSHG AHGVAVAADL

KSTQEAINKI TKNLNSLSEL EVKNLQRLSG AMDELHNEIL

ELDEKVDDLR ADTISSQIEL AVLLSNEGII NSEDEHLLAL

ERKLKKMLGP SAVEIGNGCF ETKHKCNQTC LDRIAAGTFD

AGEFSLPTFD SLNITAASLN DDGLDNHTIL LYYSTAASSL

AVTLMIAIFV VYMVSRDNVS CSICL

SEQ ID NO: 7:
HA2 portion of SEQ ID NO: 3
GFFGAIAG FLEGGWEGMI AGWHGYTSHG AHGVAVAADL

KSTQEAINKI TKNLNSLSEL EVKNLQRLSG AMDELHNEIL

ELDEKVDDLR ADTISSQIEL AVLLSNEGII NSEDEHLLAL

ERKLKKMLGP SAVEIGNGCF ETKHKCNQTC LDRIAAGTFD

AGEFSLPTFD SLNITAASLN DDGLDNHTIL LYYSTAASSL

AVTLMIAIFV VYMVSRDNVS CSICL

SEQ ID NO: 4:
HA of ICV C/Johannesburg/1/1966 (Accession No.
CAL69520; Crescenzo-Chaigne et al., J. Virol.
81, 11282-11289, 2007)
MFFSLLLVLG LTEAEKIKIC LQKQVNSSFS LHNGFGGNLY

ATEEKRMFEL VKPKAGASVL NQSTWIGFGD SRTDKSNSAF

PRSADVSAKT ADKFRSLSGG SLMLSMFGPP GKVDYLYQGC

GKHKVFYEGV NWSPHAAINC YRKNWTDIKL NFQKNIYELA

SQSHCMSLVN ALDKTIPLQV TAGTAGNCNN SFLKNPALYT

QEVKPSENKC GKENLAFFTL PTQFGTYECK LHLVASCYFI

YDSKEVYNKR GCDNYFQVIY DSSGKVVGGL DNRVSPYTGN

SGDTPTMQCD MLQLKPGRYS VRSSPRFLLM PERSYCFDMK

EKGPVTAVQS IWGKGRESDY AVDQACLSTP GCMLIQKQKP

YIGEADDHHG DQEMRELLSG LDYEARCISQ SGWVNETSPF

TEKYLLPPKF GRCPLAAKEE SIPKIPDGLL IPTSGTDTTV

TKPKSRIFGI DDLIIGLLFV AIVETGIGGY LLGSRKESGG

GVTKESAEKG FEKIGNDIQI LKSSINIAIE KLNDRISHDE

QAIRDLTLEI ENARSEALLG ELGIIRALLV GNISIGLQES

LWELASEITN RAGDLAVEVS PGCWIIDNNI CDQSCQNFIF

KFNETAPVPT IPPLDTKIDL QSDPFYWGSS LGLAITATIS

LAALVISGIA ICRTK

SEQ ID NO: 8: HA2 portion of SEQ ID NO: 4
GDQEMRELLSG LDYEARCISQ SGWVNETSPF TEKYLLPPKF

GRCPLAAKEE SIPKIPDGLL IPTSGTDTTV TKPKSRIFGI

DDLIIGLLFV AIVETGIGGY LLGSRKESGG GVTKESAEKG

FEKIGNDIQI LKSSINIAIE KLNDRISHDE QAIRDLTLEI

ENARSEALLG ELGIIRALLV GNISIGLQES LWELASEITN

RAGDLAVEVS PGCWIIDNNI CDQSCQNFIF KFNETAPVPT

IPPLDTKIDL QSDPFYWGSS LGLAITATIS LAALVISGIA ICRTK
```

In addition to the exemplified HA proteins from which some engineered HA proteins of the invention are derived, some other engineered influenza HA proteins of the invention can be derived from HA protein sequences that are substantially identical to one of these exemplified sequences, including conservatively modified variant sequences. Beyond the specific amino acid substitutions noted above, one can readily determine other residues in the wildtype HA sequences that can tolerate changes. Again, this can be achieved via sequence alignment and also considering conserved influenza HA motifs and residues known in the art.

The various engineered influenza HA proteins of the invention can be obtained or generated in accordance with the protocols exemplified herein or methods well known in the art. See, e.g., Sambrook et al., Molecular Cloning: A Laboratory Manual, Cold Spring Harbor Press, N.Y., (3$^{rd}$ ed., 2000); and Brent et al., Current Protocols in Molecular Biology, John Wiley & Sons, Inc. (ringbou ed., 2003). Upon recombinant expression (e.g., in ExpiCHO cells as detailed herein), the proteins can be purified by any of the routinely practiced procedures. See, e.g., Guide to Protein Purification, Ed. Deutscher, Meth. Enzymol. 185, Academic Press, San Diego, 1990; and Scopes, Protein Purification: Principles and Practice, Springer Verlag, New York, 1982. Substantial purification denotes purification from other proteins or cellular components. A substantially purified protein is at least 60%, 70%, 80%, 90%, 95% or 98% pure. Once purified, antigenicity and other properties of the engineered influenza HA proteins can also be readily examined with standard methods, e.g., antigenic profiling using known bNAbs and non-NAbs, differential scanning calorimetry (DSC), electron microscopy, binding analysis via ELISA, Biolayer Interferometry (BLI), Surface Plasmon Resonance (SPR), and co-crystallography analysis as exemplified herein.

IV. Scaffolded Influenza HA Protein Compositions

The invention provides influenza HA based vaccine compositions that contain a heterologous scaffold presenting or incorporating an engineered influenza HA protein described herein. Any heterologous scaffold can be used to present the engineered influenza HA protein in the construction of the vaccines of the invention. These include nanoparticles, virus-like particles, protein carriers (e.g., immunoglobulin chains or domains such as Fc, KLH, BSA, tetanus toxoid, and diphtheria toxoid), as well as various chemical scaffolds. In some embodiments, a virus-like particle (VLP) such as bacteriophage Q$_\beta$ VLP and nanoparticles can be used. In some preferred embodiments, the heterologous scaffold for presenting or displaying the engineered influenza HA protein is a nanoparticle. Various nanoparticle platforms can be employed in generating the vaccine compositions of the invention. In general, the nanoparticles employed in the invention need to be formed by multiple copies of a single subunit.

In some preferred embodiments, the engineered influenza HA protein is presented on self-assembling nanoparticles such as self-assembling nanoparticles derived from E2p, 13-01v9 and ferritin (FR). E2p is a redesigned variant of dihydrolipoyl acyltransferase from *Bacillus stearothermophilus* that has been shown to self-assemble into thermostable 60-meric nanoparticle. See, e.g., He et al., Nat. Commun. 7:12041, 2016. Similarly, 13-01 is an engineered protein that can self-assemble into hyperstable nanoparticles. See, e.g., Hsia et al., Nature 535, 136-139, 2016. Ferritin is a globular protein found in all animals, bacteria, and plants. The globular form of ferritin is made up of monomeric subunit proteins (also referred to as monomeric ferritin subunits), which are polypeptides having a molecule weight of approximately 17-20 kDa. Amino acid sequences of E2p, 13-01v9 and ferritin nanoparticle subunits and some other suitable nanoparticle sequences are known in the art. Sec, e.g., WO2017/192434, WO2019/089817 and WO19/241483. Other nanoparticles or VLPs known in the art that may also be used in the practice of the invention include, e.g., *Aquifex* aeolicus lumazine synthase, *Thermotoga Maritima* encapsulin, *Myxococcus xanthus* encapsulin, bacteriophage Qbeta virus particle, Flock House Virus (FHV) particle, ORSAY virus particle, and infectious bursal disease virus (IBDV) particle. In still some other embodiments, the scaffold for presenting the engineered influenza HA protein of the invention can further include molecules with the following PDB IDs: 1JIG (12-mer Dlp-2 from *Bacillus anthracis*), 1UVH (12-mer DPS from Mycrobacterium smegmatis), 2YGD (24-mer eye lens chaperone aB-crystallin), 3CSO (24-mer DegP24), 3MH6 and 3MH7 (24-mer HtrA proteases), 3PV2 (12-mer HtrA homolog DegQ WT), 4A8C (12-mer DegQ from *E. Coli.*), 4A9G (24-mer DegQ from *E. Coli.*), 4EVE (12-mer HP-NAP from *Helicobacter pylori* strain YS29), and 4GQU (24-mer HisB from *Mycobacterium tuberculosis*). In various embodiments, the nanoparticle vaccines of the invention can employ any of these known scaffolds, as well as their conservatively modified variants or variants with substantially identical (e.g., at least 90%, 95% or 99% identical) sequences.

In some embodiments, the influenza HA protein to be displayed on a nanoparticle platform may optionally contain a trimerization motif, e.g., SHP or foldon as exemplified herein. Some influenza nanoparticle vaccine compositions can additionally contain other structural components that function to further enhance stability and antigenicity of the displayed immunogen. In some embodiments, a locking protein domain can be inserted into the nanoparticle construct, e.g., by covalently fused to the C-terminus of the nanoparticle subunit. The locking domain can be any dimeric protein that is capable of forming an interface through specific interactions such as hydrophobic (van der Waals) contacts, hydrogen bonds, and/or salt bridges. General guidance on selecting locking domains and specific examples are described in the art, e.g., PCT2019/036917.

In some embodiments, scaffolded influenza vaccines of the invention can also contain a T-cell epitope to promote robust T-cell responses and to steer B cell development towards bNAbs. The T-cell epitope can be located at any position in relation to the other structural components as long as it does not impact presentation of the engineered HA protein on the nanoparticle surface. Any T-cell epitope sequences or peptides known in the art may be employed in the practice of the present invention. They include any polypeptide sequence that contain MHC class-II epitopes and can effectively activate CD4+ and CD8+ T cells upon immunization, e.g., T-helper epitope that activates CD4+ T helper cells. Sec, e.g., Alexander et al., Immunity 1, 751-761,1994; Ahlers et al., J. Clin. Invest. 108:1677-1685, 2001; Fraser et al., Vaccine 32, 2896-2903, 2014; De Groot et al., Immunol. Cell Biol. 8:255-269, 2002; and Gene Ther. 21:225-232, 2014. In some embodiments, the T cell epitope inserted into the nanoparticle vaccine construct is a universal pan DR epitope peptide (PADRE). See, e.g., Hung et al., Mole. Ther. 15:1211-19, 2007; Wu et al., J. Biomed. Sci. 17:88, 2010; and Bissati et al., npj Vaccines 2:24, 2017. Other examples of suitable T-cell epitope are also described in the art, e.g., the D and TpD epitope (Fraser et al., Vaccine 32, 2896-2903, 2014).

The scaffolded influenza vaccine compositions of the invention can be constructed in accordance with standard recombinant techniques and other methods that have been described in the art, e.g., He et al., Nat. Comm. 7, 12041, 2016; Kong et al., Nat. Comm. 7, 12040, 2016; He et al., Sci Adv. 4 (11): eaau6769, 2018; and PCT publications WO2017/192434, WO2019/089817 and WO19/241483. In various embodiments, nanparticles displaying any of the engineered influenza HA proteins can be constructed by fusing the influenza HA protein to the subunit of the nanoparticle (e.g., E2p subunit). Preferably, C-terminus of the influenza HA protein sequence is fused to the N-terminus of the nanoparticle subunit sequence. In some embodiments, a short peptide spacer can be used to connect the influenza HA protein sequence and the nanoparticle subunit sequence.

V. Polynucleotides and Expression Constructs

The engineered influenza HA proteins and the scaffolded vaccine compositions of the invention are typically produced by first generating expression constructs (i.e., expression vectors) that contain operably linked coding sequences of the various structural components described herein. Accordingly, in some related aspects, the invention provides polynucleotides (e.g., DNA or RNA) that encode the engineered influenza HA proteins or polypeptides, and that encode the subunit sequence of nanoparticle-displayed influenza HA proteins, as well as expression vectors that harbor such polynucleotides and host cells for producing the engineered influenza HA proteins and the vaccine compositions (e.g., ExpiCHO cells as exemplified herein). The fusion polypeptides encoded by the polynucleotides or expressed from the vectors are also encompassed by the invention.

The polynucleotides and related vectors can be readily generated with standard molecular biology techniques or the protocols exemplified herein. For example, general protocols for cloning, transfecting, transient gene expression and obtaining stable transfected cell lines are described in the art, e.g., Sambrook et al., Molecular Cloning: A Laboratory Manual, Cold Spring Harbor Press, N.Y., ($3^{rd}$ ed., 2000); and Brent et al., Current Protocols in Molecular Biology, John Wiley & Sons, Inc. (ringbou edition, 2003). Introducing mutations to a polynucleotide sequence by PCR can be performed as described in, e.g., PCR Technology: Principles and Applications for DNA Amplification, H. A. Erlich (Ed.), Freeman Press, NY, NY, 1992; PCR Protocols: A Guide to Methods and Applications, Innis et al. (Ed.), Academic Press, San Diego, C A, 1990; Mattila et al., Nucleic Acids Res. 19:967, 1991; and Eckert et al., PCR Methods and Applications 1:17, 1991.

The selection of a particular vector depends upon the intended use of the fusion polypeptides. For example, the selected vector must be capable of driving expression of the fusion polypeptide in the desired cell type, whether that cell type be prokaryotic or eukaryotic. Many vectors contain sequences allowing both prokaryotic vector replication and eukaryotic expression of operably linked gene sequences. Vectors useful for the invention may be autonomously replicating, that is, the vector exists extrachromosomally and its replication is not necessarily directly linked to the replication of the host cell's genome. Alternatively, the replication of the vector may be linked to the replication of the host's chromosomal DNA, for example, the vector may be integrated into the chromosome of the host cell as achieved by retroviral vectors and in stably transfected cell lines. Both viral-based and nonviral expression vectors can be used to produce the immunogens in a mammalian host cell. Non-viral vectors and systems include plasmids, episomal vectors, typically with an expression cassette for expressing a protein or RNA, and human artificial chromosomes (see, e.g., Harrington et al., Nat. Genet. 15:345, 1997). Useful viral vectors include vectors based on lentiviruses or other retroviruses, adenoviruses, adenoassociated viruses, cytomegalovirus, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

Depending on the specific vector used for expressing the fusion polypeptide, various known cells or cell lines can be employed in the practice of the invention. The host cell can be any cell into which recombinant vectors carrying a fusion of the invention may be introduced and wherein the vectors are permitted to drive the expression of the fusion polypeptide is useful for the invention. It may be prokaryotic, such as any of a number of bacterial strains, or may be eukaryotic, such as yeast or other fungal cells, insect or amphibian cells, or mammalian cells including, for example, rodent, simian or human cells. Cells expressing the fusion polypeptides of the invention may be primary cultured cells or may be an established cell line. Thus, in addition to the cell lines exemplified herein (e.g., CHO cells), a number of other host cell lines capable well known in the art may also be used in the practice of the invention. These include, e.g., various Cos cell lines, HeLa cells, HEK293, AtT20, BV2, and N18 cells, myeloma cell lines, transformed B-cells and hybridomas.

The use of mammalian tissue cell culture to express polypeptides is discussed generally in, e.g., Winnacker, From Genes to Clones, VCH Publishers, N. Y., N.Y., 1987. The fusion polypeptide-expressing vectors may be introduced to the selected host cells by any of a number of suitable methods known to those skilled in the art. For the introduction of fusion polypeptide-encoding vectors to mammalian cells, the method used will depend upon the form of the vector. For plasmid vectors, DNA encoding the fusion polypeptide sequences may be introduced by any of a number of transfection methods, including, for example, lipid-mediated transfection ("lipofection"), DEAE-dextran-mediated transfection, electroporation or calcium phosphate precipitation. These methods are detailed, for example, in Brent et al., supra. Lipofection reagents and methods suitable for transient transfection of a wide variety of transformed and non-transformed or primary cells are widely available, making lipofection an attractive method of introducing constructs to eukaryotic, and particularly mammalian cells in culture. For example, LipofectAMINE™ (Life Technologies) or LipoTaxi™ (Stratagene) kits are available. Other companies offering reagents and methods for lipofection include Bio-Rad Laboratories, Clontech, Glen Research, Life Technologies, JBL Scientific, MBI Fermentas, Pan Vera, Promega, Quantum Biotechnologies, Sigma-Aldrich, and Wako Chemicals USA.

For long-term, high-yield production of recombinant fusion polypeptides, stable expression is preferred. Rather than using expression vectors which contain viral origins of replication, host cells can be transformed with the fusion polypeptide-encoding sequences controlled by appropriate expression control elements (e.g., promoter, enhancer, sequences, transcription terminators, polyadenylation sites, etc.), and selectable markers. The selectable marker in the recombinant vector confers resistance to the selection and allows cells to stably integrate the vector into their chromosomes. Commonly used selectable markers include neo, which confers resistance to the aminoglycoside G-418 (Colberre-Garapin, et al., J. Mol. Biol., 150:1, 1981); and hygro, which confers resistance to hygromycin (Santerre et al., Gene, 30:147, 1984). Through appropriate selections, the transfected cells can contain integrated copies of the fusion polypeptide encoding sequence.

VI. Pharmaceutical Compositions and Therapeutic Applications

The invention provides pharmaceutical or immunogenic compositions and related methods of using the engineered influenza HA proteins and nanoparticles displaying the engineered HA proteins as described herein for preventing and treating influenza infections (e.g., flu). In some embodiments, an engineered influenza HA sequence (a polypeptide or a polynucleotide sequence) or a nanoparticle displaying an engineered protein is included in the pharmaceutical composition. The pharmaceutical composition can be either a therapeutic formulation or a prophylactic formulation. Typically, the composition additionally includes one or more pharmaceutically acceptable vehicles and, optionally, other therapeutic ingredients (for example, antibiotics or antiviral drugs). Various pharmaceutically acceptable additives can also be used in the compositions.

Some of the pharmaceutical compositions of the invention are vaccines. For vaccine compositions, appropriate adjuvants can be additionally included. Examples of suitable adjuvants include, e.g., aluminum hydroxide, lecithin, Freund's adjuvant, MPL™ and IL-12. In some embodiments, the engineered influenza HA proteins and related vaccines as disclosed herein can be formulated as a controlled-release or time-release formulation. This can be achieved in a composition that contains a slow release polymer or via a microencapsulated delivery system or bioadhesive gel. The various ppharmaceutical compositions can be prepared in accordance with standard procedures well known in the art. See, e.g., Remington's Pharmaceutical Sciences, 19.sup.th Ed., Mack Publishing Company, Easton, Pa., 1995; Sustained and Controlled Release Drug Delivery Systems, J. R. Robinson, ed., Marcel Dekker, Inc., New York, 1978); U.S. Pat. Nos. 4,652,441 and 4,917,893; 4,677,191 and 4,728, 721; and 4,675,189.

Therapeutic methods of the invention involve administering an engineered influenza HA molecule (a protein or a nucleic acid) of the invention or a pharmaceutical composition containing the molecule to a subject having or at risk of developing an influenza infection (e.g., flu). Typically, the immunogenic composition of the invention is administered in an amount sufficient to induce an immune response against an influenza virus or a group of viruses. For prophylactic applications, the immunogenic composition is provided in advance of any symptom, for example in advance of infection. The prophylactic administration of the immunogenic compositions serves to prevent or ameliorate any subsequent infection. Thus, in some embodiments, a subject to be treated is one who has, or is at risk for developing, an influenza viral infection, for example because of exposure or the possibility of exposure to a virus. Following administration of a therapeutically effective amount of the disclosed therapeutic compositions, the subject can be monitored for viral infection, symptoms associated with influenza viral infection, or both. For therapeutic applications, the immunogenic composition is provided at or after the onset of a symptom of disease or infection, for example after development of a symptom of flu, or after diagnosis of an influenza viral infection. The immunogenic composition can thus be provided prior to the anticipated exposure to a virus in order to attenuate the anticipated severity, duration or extent of an infection and/or associated disease symptoms, after exposure or suspected exposure to the virus, or after the actual initiation of an infection. The appropriate amount of an engineered HA protein or a related nanoparticle composition can be determined based on the specific disease or condition to be treated or prevented, severity, age of the subject, and other personal attributes of the specific subject (e.g., the general state of the subject's health and the robustness of the subject's immune system). Determination of effective dosages is additionally guided with animal model studies followed up by human clinical trials and is guided by administration protocols that significantly reduce the occurrence or severity of targeted disease symptoms or conditions in the subject.

The pharmaceutical composition of the invention can be combined with other agents known in the art for treating or preventing influenza viral infections. Administration of the pharmaceutical compositions and the known anti-viral agents can be either concurrently or sequentially. Pharmaceutical compositions containing an engineered influenza HA protein or nanoparticle vaccine of the invention can be provided as components of a kit. Optionally, such a kit includes additional components including packaging, instructions and various other reagents, such as buffers, substrates, antibodies or ligands, such as control antibodies or ligands, and detection reagents. An optional instruction sheet can be additionally provided in the kits.

EXAMPLES

The following examples are offered to illustrate, but not to limit the present invention.

Example 1 Analysis of Hemagglutinin (HA) Metastability

Figure 1B:
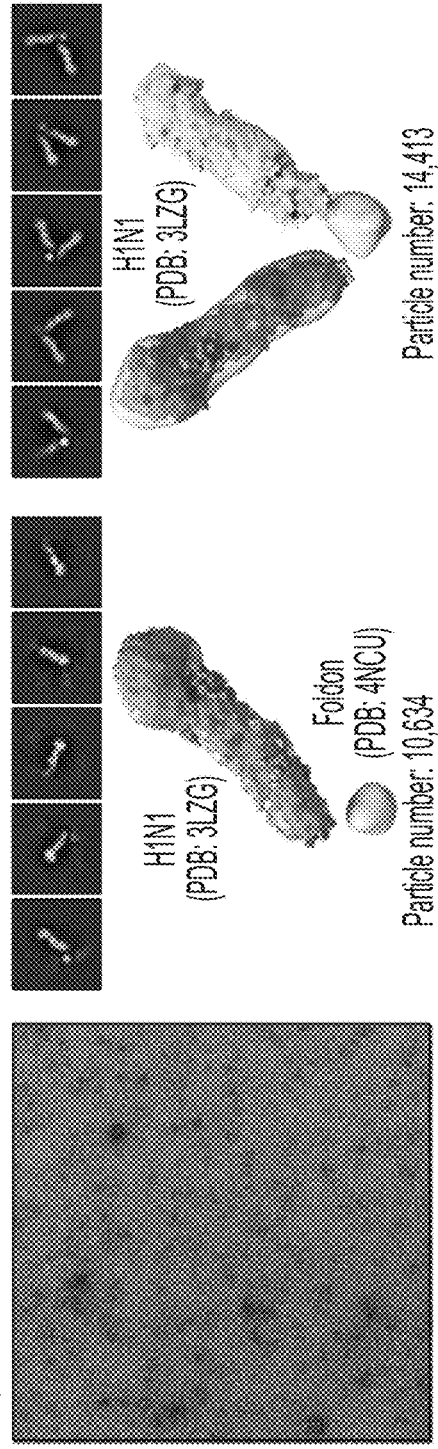
Figure 1C:
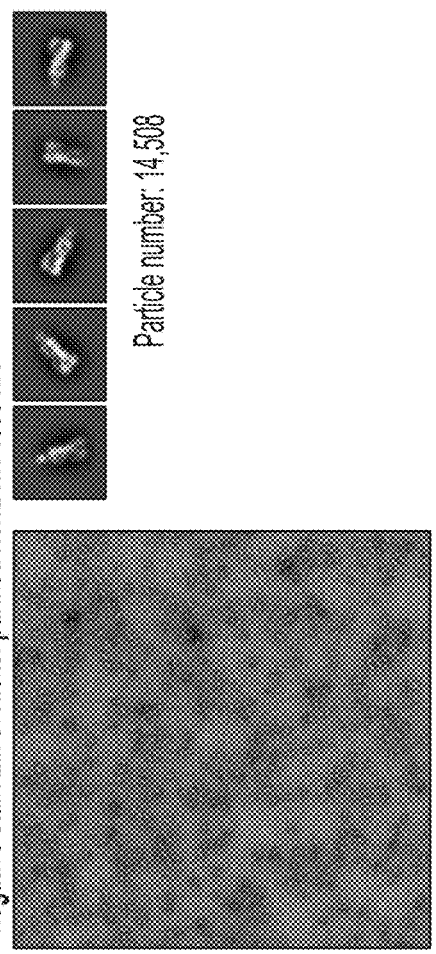

In the current study, we designed six soluble constructs for HAs from four IAV subtypes (H1, H3, H5, and H7) and two IBVs. Each HA construct encodes HA1, HA2 ectodomain, a restriction site (AS), foldon, and a $His_6$ tag. The HA2 ectodomain stops at D518 for IAV A/California/04/2009 H1N1 and at K519 for IAV A/Hong Kong/1/1968 H3N2 (GenBank: CY044261), respectively. These HA constructs were expressed transiently in ExpiCHO cells and purified using Nickel column and antibody columns, followed by size-exclusion chromatography (SEC) on a Superdex 200 10/300 column (FIG. 1A). Overall, a trimer peak was observed for all HAs tested, irrespective of the purification method. Notably, all HAs from Group-1 IAVs and the IBV Victoria lineage showed a trimer peak at 10.7-10.9 ml, whereas all HAs from Group-2 IAVs and the IBV Yamagata lineage showed a trimer peak at 11.1-11.7 ml, indicating a difference in molecular size. Negative-stain EM was performed to assess H1N1 (FIG. 1B) and H3N2 (FIG. 1C) HAs. Indeed, H1N1 HAs appeared to be open trimers, whereas H3N2 HAs were closed trimers that fit well with the crystal structure (PDB ID: 4FNK). Thus, "open trimer" seems to be a major form of metastability for H1 HAs.

Figure 2A:
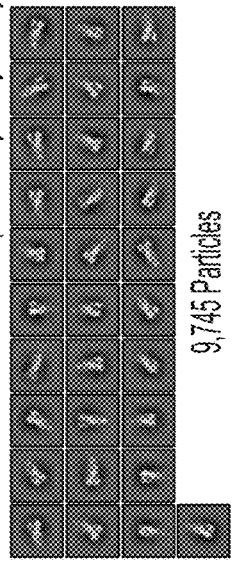
FIGS. 2A-2B show results of negative-stain EM analysis of H5N1 and H7N9 HA proteins.
Figure 2A:
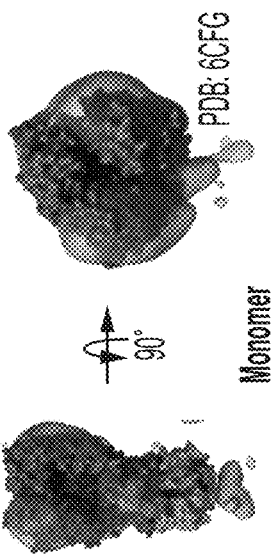
Figure 2A:
Figure 2A:
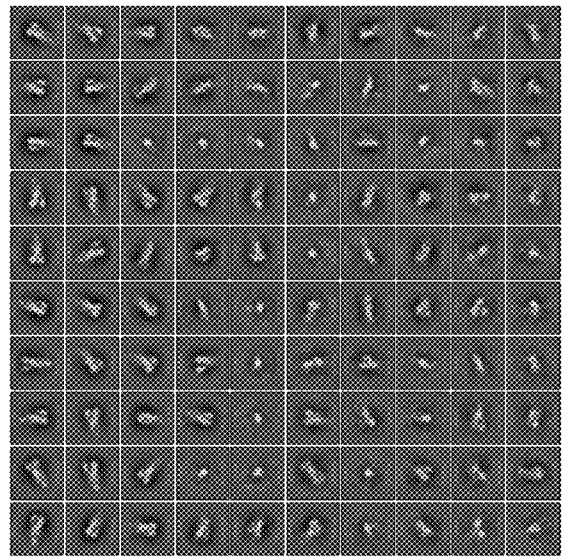
Figure 2A:
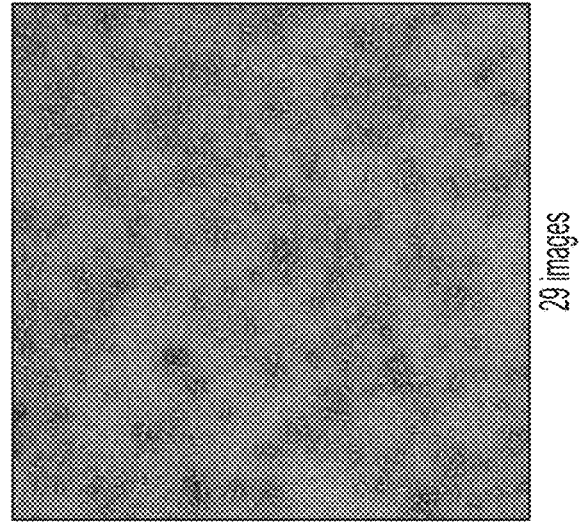
Figure 2B:
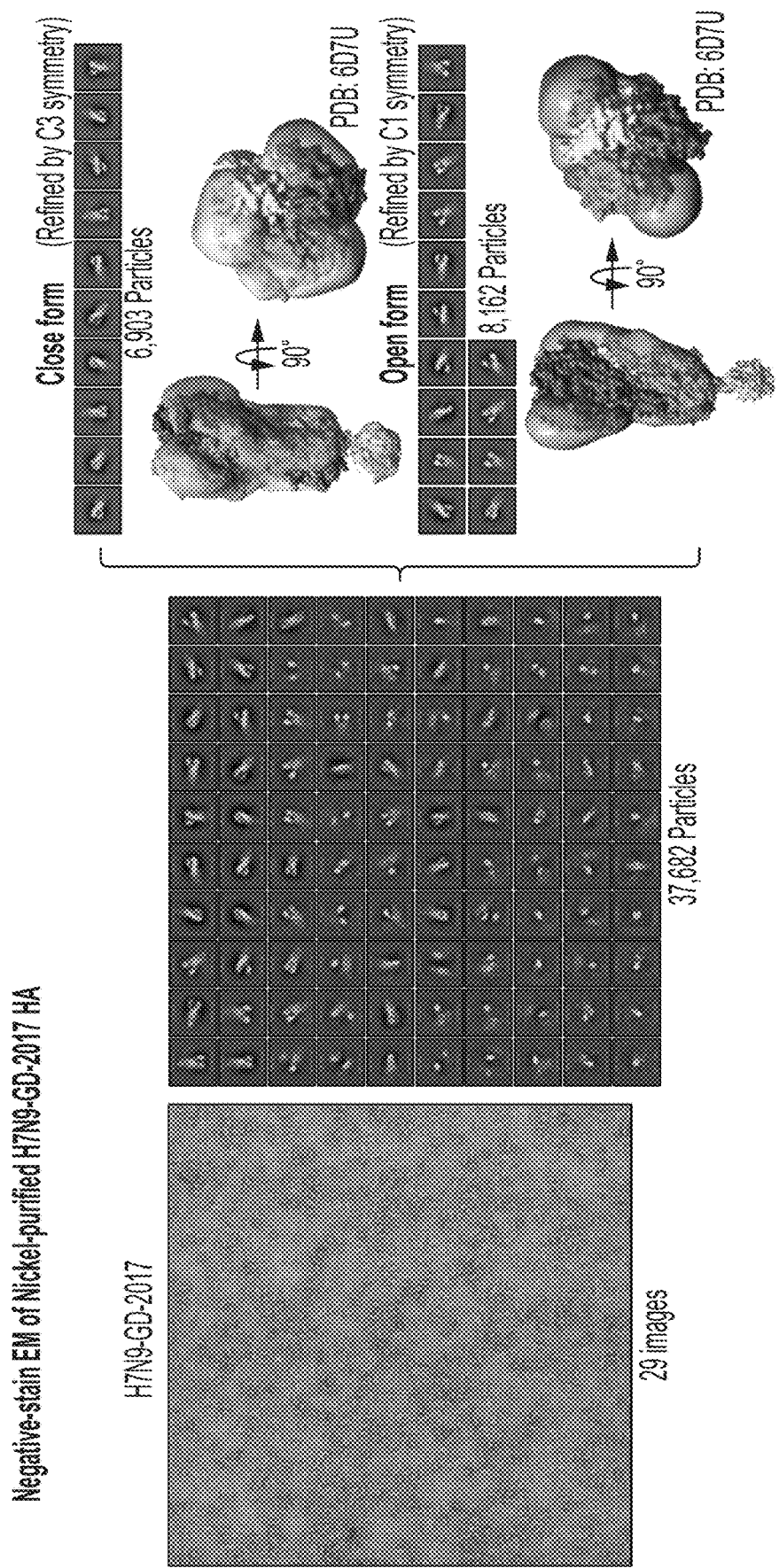

We analyzed the H5N1 and H7N9 HAs in depth by SEC and negative-stain EM. Similarly, the HA construct encodes HA1, HA2 ectodomain, AS, foldon, and a $His_6$ tag. Of note, the HA2 ectodomain stops at S520 for A/Viet Nam/1203/2004 H5N1 (GenBank: AY818135) and at D513 for IAV A/Guangdong/HP001/2017 H7N9 (GenBank: KY643843), respectively. These HA constructs were expressed transiently in ExpiCHO cells and purified using the Nickel column or antibody columns, followed by SEC using a Superdex 200 10/300 column, as shown in FIG. 1A. As described above, the H5N1 HA and H7N9 HA displayed trimer peaks at 10.9 and 11.7 ml, respectively. Negative-stain EM was then performed to assess H5N1-VN-2004 (FIG. 2A) and H7N9-GD-2017 (FIG. 2B) HAs. For the H5N1 HA, we observed greater flexibility for the HA2 region in the 2D class images (FIG. 2A, middle). As a result, applying C3 symmetry did not result in reasonable 3D reconstruction of the HA trimer. Even when the C1 symmetry was enforced, the 3D model showed less resolved density for the bottom portion of the HA trimer (FIG. 2A, right). A small fraction of HA proteins appeared to be monomers (FIG. 2A, right, bottom). For the H7N9 HA, we observed a clear pattern of dissociated head domains (FIG. 2B, middle). Less than 50% of the HA proteins were closed trimers and allowed 3D reconstruction of a complete trimer model (FIG. 2B, right, top). In contrast, more than 50% of the HA proteins could only be analyzed by enforcing the C1 symmetry, resulting in a 3D model with two HA protomers (FIG. 2B, right bottom). In summary, our EM analysis showed other forms of HA metastability for H5 and H7.

Example 2 Identification of the Causes of Hemagglutinin (HA) Metastability

To identify the causes of HA metastability, we aligned the HA2 ectodomains of 10 HAs from four IAV subtypes (H1, H3, H5 and H7) and 2 IBV lineages (Victoria and Yamagata) (FIG. 3A). We identified several positions that may contribute to the HA metastability according to the widely-used H3 numbering system. First, we hypothesize that a polar/charged residue at position 95 is the fundamental cause of HA metastability because it is located toward the C-terminal end of the C helix in the center of the HA trimer and forms repulsive polar-polar interactions (FIG. 3B). We analyzed 15821, 12493, and 7081 non-redundant HA sequences of human, avian, and swain origins from the NCBI Influenza Virus Resource website and found that the presence of a polar/charged residue is conserved across the database. Second, we hypothesize that position 106 in diverse HA sequences, R106 (Group-1 IAVs)/H106 (Group-2 IA Vs)/G106 (IBVs), may be another cause of HA metastability because it is positioned as the first residue of the connecting fragment between the C helix and D helix and defines subtype/type-specific properties (FIG. 3C). For Group-1 IAVs, R106 forms repulsive interactions that force the HA trimer to open, whereas for Group-2 IAVs, the sidechain of H106 packs against the sidechains of K51 and Q105 from a neighboring protomer and serves as a pH sensor to enable conditional opening of the HA trimer. For IBVs, G106 increases the flexibility of the D helix. Third, we hypothesize that the K51/E103 pair (Milder et al, Proc. Natl. Acad. Sci. USA 2022, 119: e2115379119) can be mutated to hydrophobic residues to stabilize the packing between the A helix and C helix (FIG. 3D). This salt bridge was recently proposed as a pH sensor and mutated to stabilize HA. However, the H1N1 HA-K51I/E103I mutant displayed an open conformation in the negative-stain EM analysis reported by Midler et al. Notably, this hypothetic pH sensor only exists in IAV HAs. In summary, position 95 is most critical to HA metastability and can be mutated to a hydrophobic residue (e.g., Ala, Val, Leu, Ile, Met, Phe, Tyr, and Trp), which can be used alone or with a hydrophobic mutation at position 106 or at K51/E103 to stabilize HA trimers. All residues in this section are numbered according to the alignment to H3 HA, or H3 numbering system.

Figure 4B:
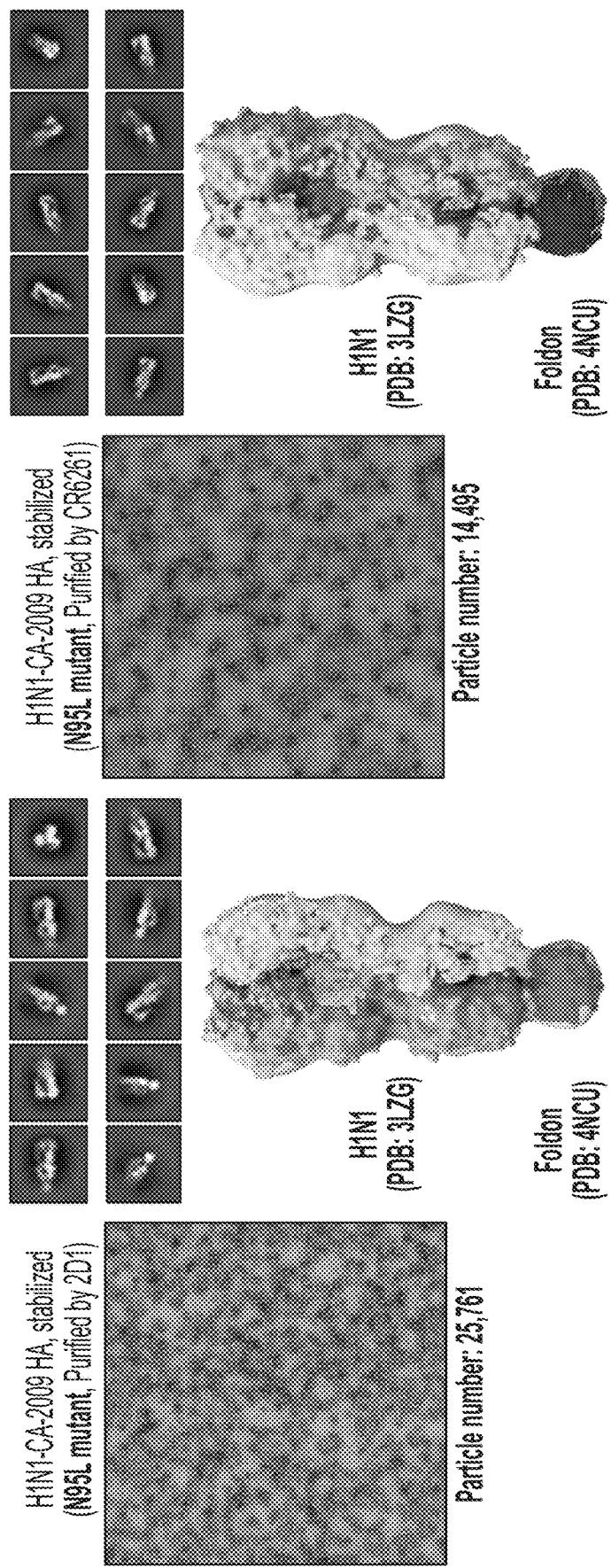

Example 3 Stabilization of the H1N1 Hemagglutinin (HA) Trimer by a Single N95L Mutation Given the importance of the position 95 to HA metastability, we created an HA-N95L mutant for the H1N1 pandemic strain, A/California/04/09. Following the same protocol, we expressed this HA protein transiently (and in a small scale) in ExpiCHO cells and purified it using a Nickel column and two antibody columns. The purified proteins were analyzed by SEC on a Superdex 200 10/300 column and the SEC profiles were compared with those of the wildtype HA (FIG. 4A). With the N95L mutation, the HA trimer peak shifted toward the right at 11.6-11.9 ml, compared to the trimer peaks at 10.6-10.7 ml observed for the wildtype HAs (FIG. 4A). The structure of HA-N95L mutant purified by 2D1 (head NAb) and CR6261 (stem NAb) columns was assessed by negative-stain EM (FIG. 4B). In both cases, a single mutation at N95L was found to effectively stabilize HA in a closed trimer conformation that fits well with the crystal structure (PDB ID: 3LZG) (FIG. 4B). The results thus confirmed our HA metastability hypothesis and demonstrated the utility of a hydrophobic mutation at N95L for trimer stabilization.

The invention thus has been disclosed broadly and illustrated in reference to representative embodiments described above. It is understood that various modifications can be made to the present invention without departing from the spirit and scope thereof.

It is further noted that all publications, sequence accession numbers, patents and patent applications cited herein are hereby expressly incorporated by reference in their entirety and for all purposes as if each is individually so denoted. Definitions that are contained in text incorporated by reference are excluded to the extent that they contradict definitions in this disclosure.

What is claimed is:

1. An engineered influenza viral hemagglutinin (HA) protein, comprising a modified HA2 ectodomain, wherein the modified HA2 ectodomain comprises substitution of the amino acid residue at position 95 or at position 106 with a hydrophobic residue; wherein amino acid numbering of HA2 is based on Influenza A Subtype H3.

2. The engineered influenza viral hemagglutinin (HA) protein of claim 1, further comprising an intact HA1.

3. The engineered influenza viral hemagglutinin (HA) protein of claim 1, which does not contain the HA head domain.

4. The engineered influenza viral hemagglutinin (HA) protein of claim 1, wherein the HA protein is from an influenza A virus, and the substituted amino acid residue is N95.

5. The engineered influenza viral hemagglutinin (HA) protein of claim 1, wherein the HA protein is from an influenza B virus, and the substituted amino acid residue is Q95.

6. The engineered influenza viral hemagglutinin (HA) protein of claim 1, wherein the HA protein is from an influenza C virus, and the substituted amino acid residue is E95.

7. The engineered influenza viral hemagglutinin (HA) protein of claim 1, wherein the substituting residue is Ala, Val, Leu, Ile, Met, Phe, Tyr, or Trp.

8. The engineered influenza viral hemagglutinin (HA) protein of claim 1, wherein the modified HA2 ectodomain comprises substitutions of both amino acid residue at positions 95 and 106 with a hydrophobic residue.

9. The engineered influenza viral hemagglutinin (HA) protein of claim 8, wherein (1) the HA protein is from a Group 1 influenza A virus, and the residue at position 106 is R106, (2) the HA protein is from a Group 2 influenza A virus, and the residue at position 106 is H106, or (3) the HA protein is from an influenza B virus, and the residue at position 106 is G106.

10. The engineered influenza viral hemagglutinin (HA) protein of claim 8, wherein each substitution is independently with Ala, Val, Leu, Ile, Met, Phe, Tyr, or Trp.

11. The engineered influenza viral hemagglutinin (HA) protein of claim 1, comprising (1) the substitution at position 95 and (2) additional amino acid substitution at one or both of positions 51 and 103 with a hydrophobic residue.

12. The engineered influenza viral hemagglutinin (HA) protein of claim 11, wherein the HA protein is from an influenza A virus, and the additionally substituted amino acid residues are K51 and E103.

13. The engineered influenza viral hemagglutinin (HA) protein of claim 1, further comprising the subunit sequence of a self-assembling nanoparticle that is fused to the C-terminus of the engineered HA protein.

14. A pharmaceutical composition, comprising the engineered influenza viral hemagglutinin (HA) protein of claim 1, and a pharmaceutically acceptable carrier.

15. The pharmaceutical composition of claim 14, wherein the engineered HA protein is displayed on the surface of a self-assembling nanoparticle.

16. A polynucleotide encoding the engineered influenza viral hemagglutinin (HA) protein of claim 1.

17. A vector comprising the polynucleotide of claim 14.

18. A host cell harboring the polynucleotide of claim 14.

19. An influenza viral vaccine composition, comprising the engineered HA protein of claim 1 that is displayed on the surface of a self-assembling nanoparticle.

20. The vaccine composition of claim 19, wherein the self-assembling nanoparticle comprises a trimeric sequence, and wherein C-terminus of the engineered HA protein is fused to N-terminus of the subunit sequence of the nanoparticle.

21. The vaccine composition of claim 19, wherein the self-assembling nanoparticle comprises I3-01, E2p or ferritin.

22. The vaccine composition of claim 19, further comprising a locking domain and/or a T-cell epitope that is fused to the C-terminus of the nanoparticle subunit sequence.

23. A method of treating or preventing an influenza viral infection in a subject, comprising administering to the subject the pharmaceutical composition of claim 14, thereby treating or preventing the influenza viral infection in the subject.

* * * * *

SEQUENCE LISTING

```
Sequence total quantity: 20
SEQ ID NO: 1            moltype = AA  length = 564
FEATURE                 Location/Qualifiers
source                  1..564
                        mol_type = protein
                        organism = human influenza virus
SEQUENCE: 1
MKAILVVLLY TFATANADTL CIGYHANNST DTVDTVLEKN VTVTHSVNLL EDKHNGKLCK    60
LRGVAPLHLG KCNIAGWILG NPECESLSTA SSWSYIVETP SSDNGTCYPG DFIDYEELRE   120
QLSSVSSFER FEIFPKTSSW PNHDSNKGVT AACPHAGAKS FYKNLIWLVK KGNSYPKLSK   180
SYINDKGKEV LVLWGIHHPS TSADQQSLYQ NADTYVFVGS SRYSKKFKPE IAIRPKVRDQ   240
EGRMNYYWTL VEPGDKITFE ATGNLVVPRY AFAMERNAGS GIIISDTPVH DCNTTCQTPK   300
GAINTSLPFQ NIHPITIGKC PKYVKSTKLR LATGLRNIPS IQSRGLFGAI AGFIEGGWTG   360
MVDGWYGYHH QNEQGSGYAA DLKSTQNAID EITNKVNSVI EKMNTQFTAV GKEFNHLEKR   420
NLNKKVDDGF LDIWTYNAEL LVLLENERTL DYHDSNVKNL YEKVRSQLKN NAKEIGNGCF   480
EFYHKCDNTC MESVKNGTYD YPKYSEEAKL NREEIDGVKL ESTRIYQILA IYSTVASSLV   540
LVVSLGAISF WMCSNGSLQC RICI                                         564
```

-continued

```
SEQ ID NO: 2            moltype = AA  length = 566
FEATURE                 Location/Qualifiers
source                  1..566
                        mol_type = protein
                        organism = human influenza virus
SEQUENCE: 2
MKTIIALSHI LCLVFAQKLP GNDNSTATLC LGHHAVPNGT IVKTITNDQI EVTNATELVQ  60
NSSIGEICDS PHQILDGENC TLIDALLGDP QCDGFQNKKW DLFVERSKAY SNCYPYDVPD  120
YASLRSLVAS SGTLEFNNES FNWTGVTQNG TSSACIRRSN NSFFSRLNWL TQLNFKYPAL  180
NVTMPNNEQF DKLYIWGVHH PVTDKDQIFL YAQSSGRITV STKRSQQAVI PNIGYRPRIR  240
NIPSRISIYW TIVKPGDILL INSTGNLIAP RGYFKIRSGK SSIMRSDAPI GKCNSECITP  300
NGSIPNDKPF QNVNRITYGA CPRYVKQSTL KLATGMRNVP EKQTRGIFGA IAGFIENGWE  360
GMVDGWYGFR HQNSEGRGQA ADLKSTQAAI DQINGKLNRL IGKTNEKFHQ IEKEFSEVEG  420
RIQDLEKYVE DTKIDLWSYN AELLVALENQ HTIDLTDSEM NKLFEKTKKQ LRENAEDMGN  480
GCFKIYHKCD NACIGSIRNG TYDHDVYRDE ALNNRFQIKG VELKSGYKDW ILWISFAISC  540
FLLCVALLGF IMWACQKGNI RCNICI                                       566

SEQ ID NO: 3            moltype = AA  length = 584
FEATURE                 Location/Qualifiers
source                  1..584
                        mol_type = protein
                        organism = human influenza virus
SEQUENCE: 3
MKAIIVLLMV VTSNADRICT GITSSNSPHV VKTATQGEVN VTGVIPLTTT PTKSHFANLK  60
TETRGKLCPK CLNCTDLDVA LGRPKCTGKI PSARVSILHE VRPVTSGCFP IMHDRTKIRQ  120
LPNLLRGYEH IRLSTHNVIN AENAPGGPYK IGTSGSCPNI TNGNGFFATM AWAVPKNDKN  180
KTATNPLTIE VPYICTEGED QITVWGFHSD NETQMAKLYG DSKPQKFTSS ANGVTTHYVS  240
QIGGFPNQTE DGGLPQSGRI VVDYMVQKSG KTGTITYQRG ILLPQKVWCA SGRSKVIKGS  300
LPLIGEADCL HEKYGGLNKS KPYYTGEHAK AIGNCPIWVK TPLKLANGTK YRPPAKLLKE  360
RGFFGAIAGF LEGGWEGMIA GWHGYTSHGA HGVAVAADLK STQEAINKIT KNLNSLSELE  420
VKNLQRLSGA MDELHNEILE LDEKVDDLRA DTISSQIELA VLLSNEGIIN SEDEHLLALE  480
RKLKKMLGPS AVEIGNGCFE TKHKCNQTCL DRIAAGTFDA GEFSLPTFDS LNITAASLND  540
DGLDNHTILL YYSTAASSLA VTLMIAIFVV YMVSRDNVSC SICL                   584

SEQ ID NO: 4            moltype = AA  length = 655
FEATURE                 Location/Qualifiers
source                  1..655
                        mol_type = protein
                        organism = human influenza virus
SEQUENCE: 4
MFFSLLLVLG LTEAEKIKIC LQKQVNSSFS LHNGFGGNLY ATEEKRMFEL VKPKAGASVL  60
NQSTWIGFGD SRTDKSNSAF PRSADVSAKT ADKFRSLSGG SLMLSMFGPP GKVDYLYQGC  120
GKHKVFYEGV NWSPHAAINC YRKNWTDIKL NFQKNIYELA SQSHCMSLVN ALDKTIPLQV  180
TAGTAGNCNN SFLKNPALYT QEVKPSENKC GKENLAFFTL PTQFGTYECK LHLVASCYFI  240
YDSKEVYNKR GCDNYFQVIY DSSGKVVGGL DNRVSPYTGN SGDTPTMQCD MLQLKPGRYS  300
VRSSPRFLLM PERSYCFDMK EKGPVTAVQS IWGKGRESDY AVDQACLSTP GCMLIQKQKP  360
YIGEADDHHG DQEMRELLSG LDYEARCISQ SGWVNETSPF TEKYLLPPKF GRCPLAAKEE  420
SIPKIPDGLL IPTSGTDTTV TKPKSRIFGI DDLIIGLLFV AIVETGIGGY LLGSRKESGG  480
GVTKESAEKG FEKIGNDIQI LKSSINIAIE KLNDRISHDE QAIRDLTLEI ENARSEALLG  540
ELGIIRALLV GNISIGLQES LWELASEITN RAGDLAVEVS PGCWIIDNNI CDQSCQNFIF  600
KFNETAPVPT IPPLDTKIDL QSDPFYWGSS LGLAITATIS LAALVISGIA ICRTK        655

SEQ ID NO: 5            moltype = AA  length = 222
FEATURE                 Location/Qualifiers
source                  1..222
                        mol_type = protein
                        organism = human influenza virus
SEQUENCE: 5
GLFGAIAGFI EGGWTGMVDG WYGYHHQNEQ GSGYAADLKS TQNAIDEITN KVNSVIEKMN  60
TQFTAVGKEF NHLEKRIENL NKKVDDGFLD IWTYNAELLV LLENERTLDY HDSNVKNLYE  120
KVRSQLKNNA KEIGNGCFEF YHKCDNTCME SVKNGTYDYP KYSEEAKLNR EEIDGVKLES  180
TRIYQILAIY STVASSLVLV VSLGAISFWM CSNGSLQCRI CI                     222

SEQ ID NO: 6            moltype = AA  length = 221
FEATURE                 Location/Qualifiers
source                  1..221
                        mol_type = protein
                        organism = human influenza virus
SEQUENCE: 6
GIFGAIAGFI ENGWEGMVDG WYGFRHQNSE GRGQAADLKS TQAAIDQING KLNRLIGKTN  60
EKFHQIEKEF SEVEGRIQDL EKYVEDTKID LWSYNAELLV ALENQHTIDL TDSEMNKLFE  120
KTKKQLRENA EDMGNGCFKI YHKCDNACIG SIRNGTYDHD VYRDEALNNR FQIKGVELKS  180
GYKDWILWIS FAISCFLLCV ALLGFIMWAC QKGNIRCNIC I                      221

SEQ ID NO: 7            moltype = AA  length = 223
FEATURE                 Location/Qualifiers
source                  1..223
                        mol_type = protein

```
                                     -continued
                        organism = human influenza virus
SEQUENCE: 7
GFFGAIA

```
QKAIDGVTNK VNSIIDKMNT QFEAVGREFN NLERRIENLN KKMEDGFLDV WTYNAELLVL    120
MENERTLDFH DSNVKNLYDK VRLQLRDNAK ELGNGCFEFY HKCDNECMES IRNGTYNYPQ    180
YSEEARLKRE EISG                                                     194

SEQ ID NO: 15           moltype = AA  length = 190
FEATURE                 Location/Qualifiers
source                  1..190
                        mol_type = protein
                        organism = human influenza virus
SEQUENCE: 15
KLATGMRNVP EKQTRGLFGA IAGFIENGWE GMIDGWYGFR HQNSEGTGQA ADLKSTQAAI    60
DQINGKLNRV IEKTNEKFHQ IEKEFSEVEG RIQDLEKYVE DTKIDLWSYN AELLVALENQ   120
HTIDLTDSEM NKLFEKTRRQ LRENAEDMGN GCFKIYHKCD NACIESIRNG TYDHDVYRDE   180
ALNNRFQIKG                                                          190

SEQ ID NO: 16           moltype = AA  length = 190
FEATURE                 Location/Qualifiers
source                  1..190
                        mol_type = protein
                        organism = human influenza virus
SEQUENCE: 16
KLATGMRNVP ERQTRGIFGA IAGFIENGWE GMVDGWYGFR HQNSEGRGQA ADLKSTQAAI    60
DQINGKLNRL IGKTNEKFHQ IEKEFSEVEG RIQDLEKYVE DTKIDLWSYN AELLVALENQ   120
HTIDLTDSEM NKLFEKTKKQ LRENAEDMGN GCFKIYHKCD NACMGSIRNG TYDHNVYRDE   180
ALNNRFQIKG                                                          190

SEQ ID NO: 17           moltype = AA  length = 191
FEATURE                 Location/Qualifiers
source                  1..191
                        mol_type = protein
                        organism = human influenza virus
SEQUENCE: 17
LLATGMKNVP EIPKGRGLFG AIAGFIENGW EGLIDGWYGF RHQNAQGEGT AADYKSTQSA    60
IDQITGKLNR LIEKTNQQFE LIDNEFNEVE KQIGNVINWT RDSITEVWSY NAELLVAMEN   120
QHTIDLADSE MDKLYERVKR QLRENAEEDG TGCFEIFHKC DDDCMASIRN NTYDHSKYRE   180
EAMQNRIQID P                                                        191

SEQ ID NO: 18           moltype = AA  length = 195
FEATURE                 Location/Qualifiers
source                  1..195
                        mol_type = protein
                        organism = human influenza virus
SEQUENCE: 18
LLATGMKNVP EVPKRKRTAR GLFGAIAGFI ENGWEGLIDG WYGFRHQNAQ GEGTAADYKS    60
TQSAIDQITG KLNRLIAKTN QQFKLIDNEF NEVEKQIGNV INWTRDSITE VWSYNAELLV   120
AMENQHTIDL ADSEMDKLYE RVKRQLRENA EEDGTGCFEI FHKCDDDCMA SIRNNTYDHR   180
KYREEAMQNR IQIDP                                                    195

SEQ ID NO: 19           moltype = AA  length = 194
FEATURE                 Location/Qualifiers
source                  1..194
                        mol_type = protein
                        organism = human influenza virus
SEQUENCE: 19
KLANGTKYRP PAKLLKERGF FGAIAGFLEG GWEGMIAGWH GYTSHGAHGV AVAADLKSTQ    60
EAINKITKNL NSLSELEVKN LQRLSGAMDE LHNEILELDE KVDDLRADTI SSQIELAVLL   120
SNEGIINSED EHLLALERKL KKMLGPSAVE IGNGCFETKH KCNQTCLDRI AAGTFDAGEF   180
SLPTFDSLNI TAAS                                                     194

SEQ ID NO: 20           moltype = AA  length = 194
FEATURE                 Location/Qualifiers
source                  1..194
                        mol_type = protein
                        organism = human influenza virus
SEQUENCE: 20
KLANGTKYRP PAKLLKERGF FGAIAGFLEG GWEGMIAGWH GYTSHGAHGV AVAADLKSTQ    60
EAINKITKNL NSLSELEVKN LQRLSGAMDE LHNEILELDE KVDDLRADTI SSQIELAVLL   120
SNEGIINSED EHLLALERKL KKMLGPSAVE IGNGCFETKH KCNQTCLDRI AAGTFNAGEF   180
SLPTFDSLNI TAAS                                                     194
```